United States Patent [19]

McKown et al.

[11] Patent Number: 5,146,414
[45] Date of Patent: Sep. 8, 1992

[54] METHOD AND APPARATUS FOR CONTINUOUSLY MEASURING VOLUMETRIC FLOW

[75] Inventors: Russel McKown, Dallas; Mark Yelderman; Michael Quinn, both of Plano, all of Tex.

[73] Assignee: Interflo Medical, Inc., Plano, Tex.

[21] Appl. No.: 510,897

[22] Filed: Apr. 18, 1990

[51] Int. Cl.⁵ .............................................. G01F 1/68
[52] U.S. Cl. .................................. 364/510; 128/713; 73/861.06
[58] Field of Search .................. 364/554, 510, 413.03, 364/485, 484; 128/660.01, 660.08, 691, 713; 73/861.06, 861.05

[56] References Cited

U.S. PATENT DOCUMENTS

| | | | |
|---|---|---|---|
| 3,359,974 | 12/1967 | Khalil | 128/2.05 |
| 3,940,731 | 2/1976 | Cooper et al. | 340/3 D |
| 4,217,910 | 8/1980 | Khalil | 128/670 |
| 4,236,527 | 12/1980 | Newbower et al. | 128/692 |
| 4,240,441 | 12/1980 | Khalil | 128/692 |
| 4,361,049 | 11/1982 | Volgyesi | 73/861.05 |
| 4,380,237 | 4/1983 | Newbower | 128/693 |
| 4,507,974 | 4/1985 | Yelderman | 73/861.06 |
| 4,542,748 | 9/1985 | Roy | 128/713 |
| 4,722,347 | 2/1988 | Abrams et al. | 128/663 |
| 4,733,669 | 3/1988 | Segal | 128/663 |
| 4,785,823 | 11/1988 | Eggers et al. | 128/692 |
| 4,819,655 | 4/1989 | Webler | 128/713 |
| 4,930,517 | 6/1990 | Cohen et al. | 128/671 |

OTHER PUBLICATIONS

G. N. Stewart, "The Output of the Heart in Dogs", *American Journal of Physiology*, vol. 57, pp. 27–50 (1921).

Abrams, Jerome H.; Weber, Roland E.; Holmen, Kenneth D.; *Transtracheal Doppler: A New Procedure for Continuous Cardiac Output Measurement*, Anesthesiology; Jan. 1989; 70 (1); 134–138.

Barankay, T.; Jancso, T.; Nagy, S.; Petri, G.; *Cardiac Output Estimation by a Thermodilution Method Involving Intravascular Heating and Thermistor Recording*; Acta Physiologica Scientiarium Hungaricae; 1970; Tomus 38 (2-3); 167–173.

Bassingthwaighte, James B.; Ackerman, Francis H.; Wood, Earl H.; *Applications of the Lagged Normal Density Curve as a Model for Arterial Dilution Curves*, Circulation Res., Apr. 1966; vol. 18; 398–407.

(List continued on next page.)

*Primary Examiner*—Dale M. Shaw
*Assistant Examiner*—S. A. Melnick
*Attorney, Agent, or Firm*—Philip S. Johnson; Michael P. Dunnam

[57] ABSTRACT

Method and apparatus for adapting the volumetric flow rate measurement system taught by Yelderman in U.S. Pat. No. 4,507,974 to clinical environments by reducing the effects of physiological noise. Signal processing techniques are used to characterize the background noise power spectrum of the system under test so that the effect of noise aberrations on the measured data may be eliminated and so that the predominant periodicities of the background noise spectra may be avoided. The invention further cross-correlates the input data of the system with the corresponding ouput data of the system to determine weighting values for each input frequency so that data collected at noisy frequencies is discounted. Low frequency noise or drift is also removed from the output signal by fitting the average of the output data to a quadratic function which is then subtracted from the original output signal, point by point. Finally, the processed data is fit to a lagged normal normal distribution curve in the frequency domain to solve for the parameters necessary to mathematically model the transfer function of the system. Given the input to the system as well as the frequency domain transfer function and noise data of the system, the volumetric flow of the system then may be determined for virtually any input even in very noisy environments without knowledge of the volume of the system.

79 Claims, 15 Drawing Sheets

OTHER PUBLICATIONS

Normann, R. A.; Johnson, R. W.; Messinger, J. E.; *A Continuous Cardiac Output Computer Based on Thermodilution Principles,* Annals of Biomedical Eng.; vol. 17; pp. 61-73 (1989).

Olsson, B.; Pool, J.; Vandermoten, P.; Varnauskas, E.; Wassen, R.; *Validity and Reproducibility of Determination of Cardiac Output by Thermodilution in Man,* Cardiology; vol. 55; 136-148 (1970).

Philip, James H.; Long, Michael C.; Quinn, Michael D.; Newbower, Ronald S.; *Continuous Thermal Measurement of Cardiac Output,* IEEE Transactions on Biomedical Engineering; May 1984; 31(5); 393-400.

Rosenkrantz, Jens G.; Maloney, James C.; *Pseudorandom Noise and Cross-Correlation in Indicator-Dilution Systems,* Journal Surgical Research 1976; 21(2); 105-111 (1976).

Rubin, Lawrence M.; *Electronic Augmentation of Thermodilution Techniques,* Master of Science Thesis; Massachusetts Institute of Technology; Sep. 1975; 1-156.

Wessel, Hans U.; James, Gordon W.; Paul, Milton H.; *Effects of Respiration and Circulation on Central Blood Temperature of the Dog,* Ameri Journal Physiol 1966; 211(6); 1403-1412.

Wessel, Hans V.; Paul, Milton H.; James, Gordon W.; Grahn, Allan P.; *Limitations of Thermal Dilution Curves for Cardiac Output Determinations,* Journal of Applied Phys.; vol. 30; No. 5; May 1971; pp. 643-652.

Bullock, L. E.; *Flow Measurement Using Correlation Analysis with Pseudo Random Tag,* Mass and Process Identification by Correlation and Spectral Techniques; International Symposium, U. of Bradford, England; Jan. 2-5, 1973.

Coulam, Craig M; Warner, Homer, R.; Wood, Earl H. and Bassingthwaighte, James B.; *A Transfer Function Analysis of Coronary and Renal Circulation Calculated from Upstream and Downstream Indicator-Dilution Curves,* Cir Res; Nov. 1966; vol. 19; 879-890.

Fegler, George A.; *Measurement of Cardiac Output in Anaesthetized Animals by a Thermo-dilution Method,* Quart J. Exptl Physiol; 1954; vol. 39; 153-164.

Ganz, William; Donoso, Roberto; Marcus, Harold S.; Forrester, James S. and Swan, Harold J. C.; *A New Technique for Measurement of Cardiac Output by Thermodilution in Man,* Amer. Journal of Cardiology; 1971; vol. 27; 392-396.

Hamilton, W. F.; Moore, John Walker; Kinsman, J. M. and Spurling, R. G.; *Simultaneous Determination of the Pulmonary and Systemic Circulation Times in Man and of a Figure Related to the Cardiac Output,* Am. J. Physiol; 1928; vol. 84; 338-344.

Hosie, Kenneth F.; *Thermal Dilution Technics,* Circulation Research; 1962; vol. 10; 491-504.

Keefer, J. Robert; Barash, Paul G.; *Pulmonary Artery Catheterization, Monitoring in Anesthesia and Critical Care Medicine;* New York; Churchill Livingstone; 1985; 177-228.

Khalil, H. H.; Richardson, T. Q.; Guyton, A. C.; *Measurement of Cardiac Output by Thermal-Dilution and Direct Fick Methods in Dogs,* Journal Appl Physiol; 1966; 21(3); 1131-1135.

Maseri, Attilio; Caldini, Paolo; Permutt, Solbert and Zierler, Kenneth L.; *Frequency Function of Transit Times Through Dog Pulmonary Circulation,* Cir Res; May 1970; vol. 26; 527-543.

Nicholes, K. K.; Warner, H. R.; Woods, F. H.; *A Study of Dispersion of an Indicator in the Circulation,* Ann NY Acad Sci; 1964; vol. 115; 721-737.

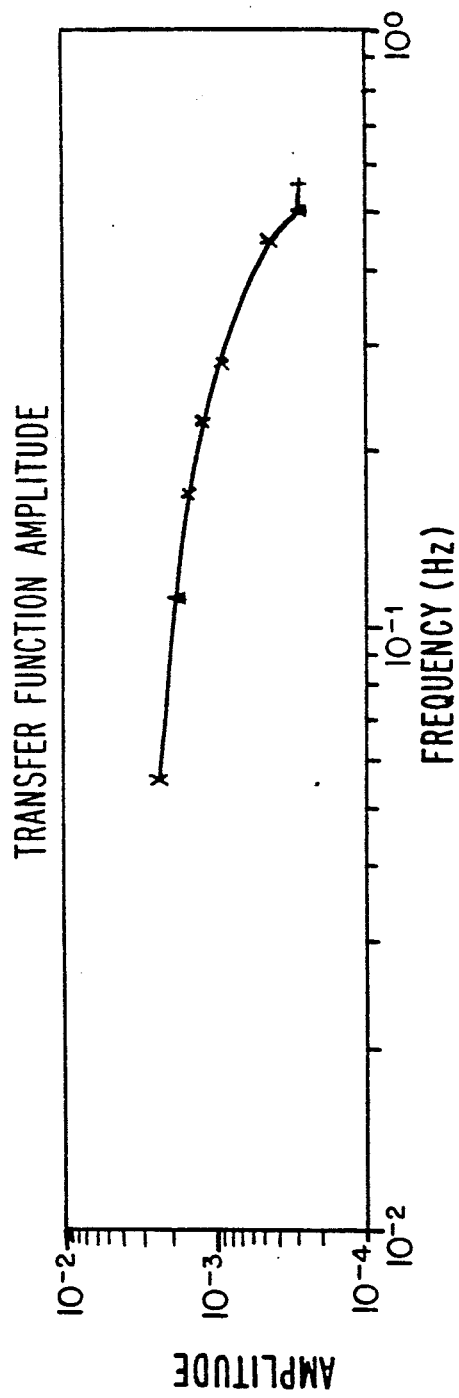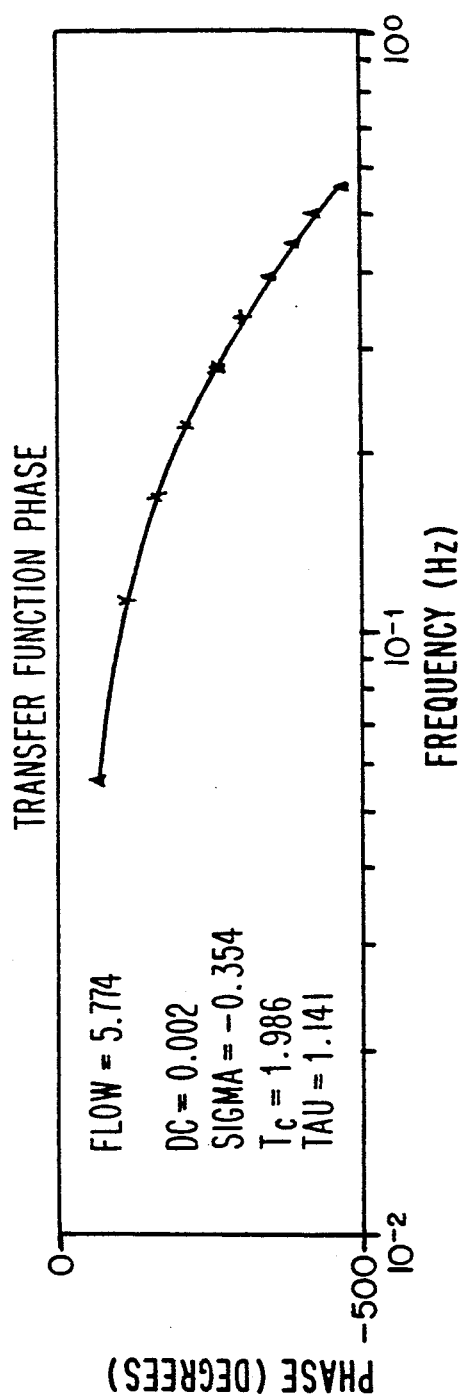
*Fig. 13a*
*Fig. 13b*

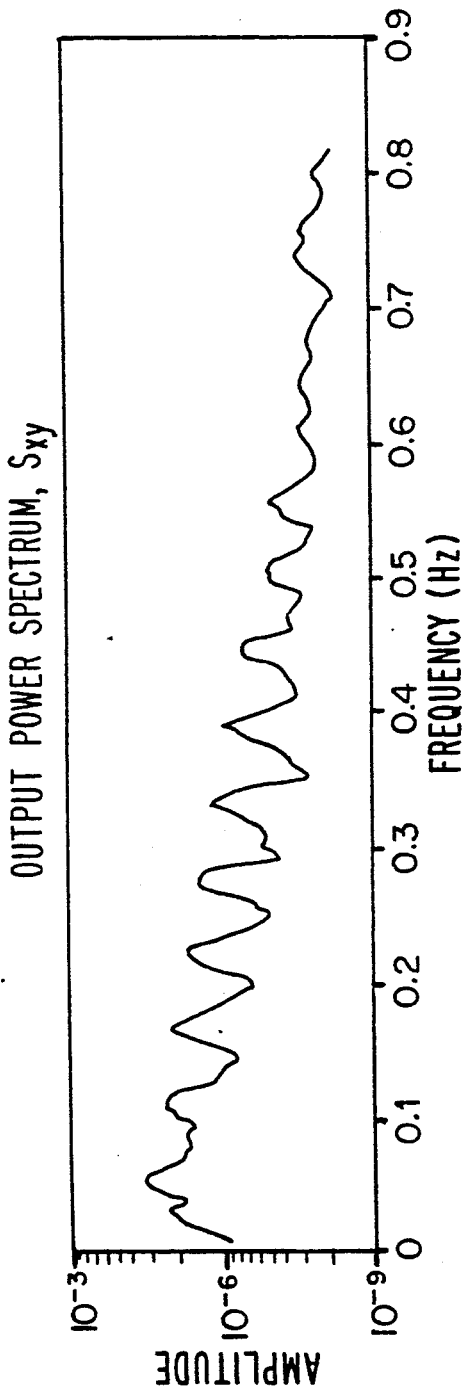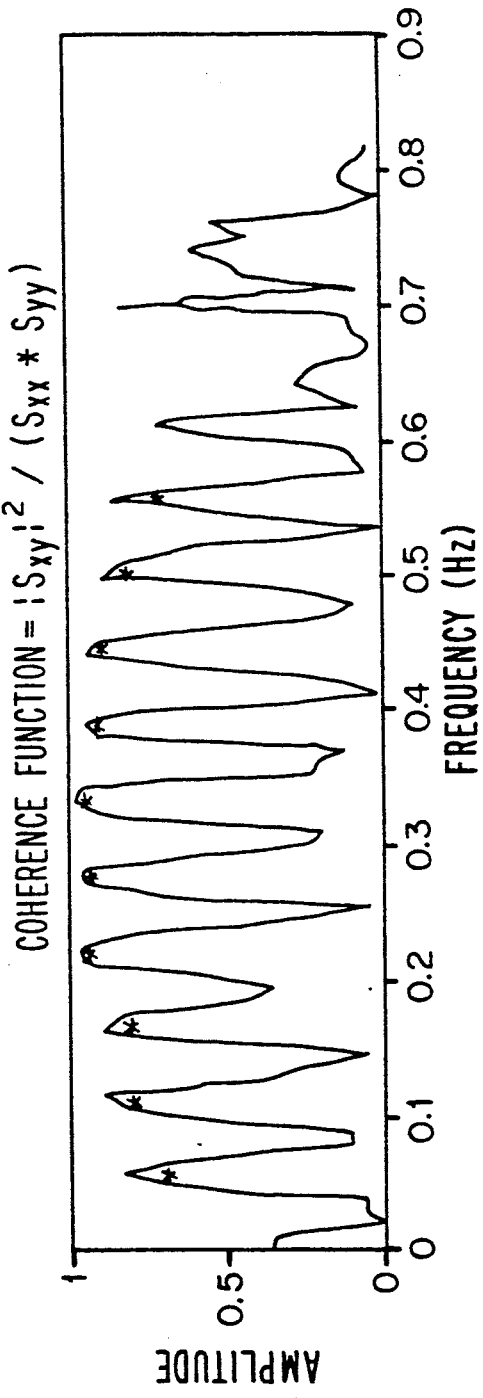
Fig. 14a
Fig. 14b

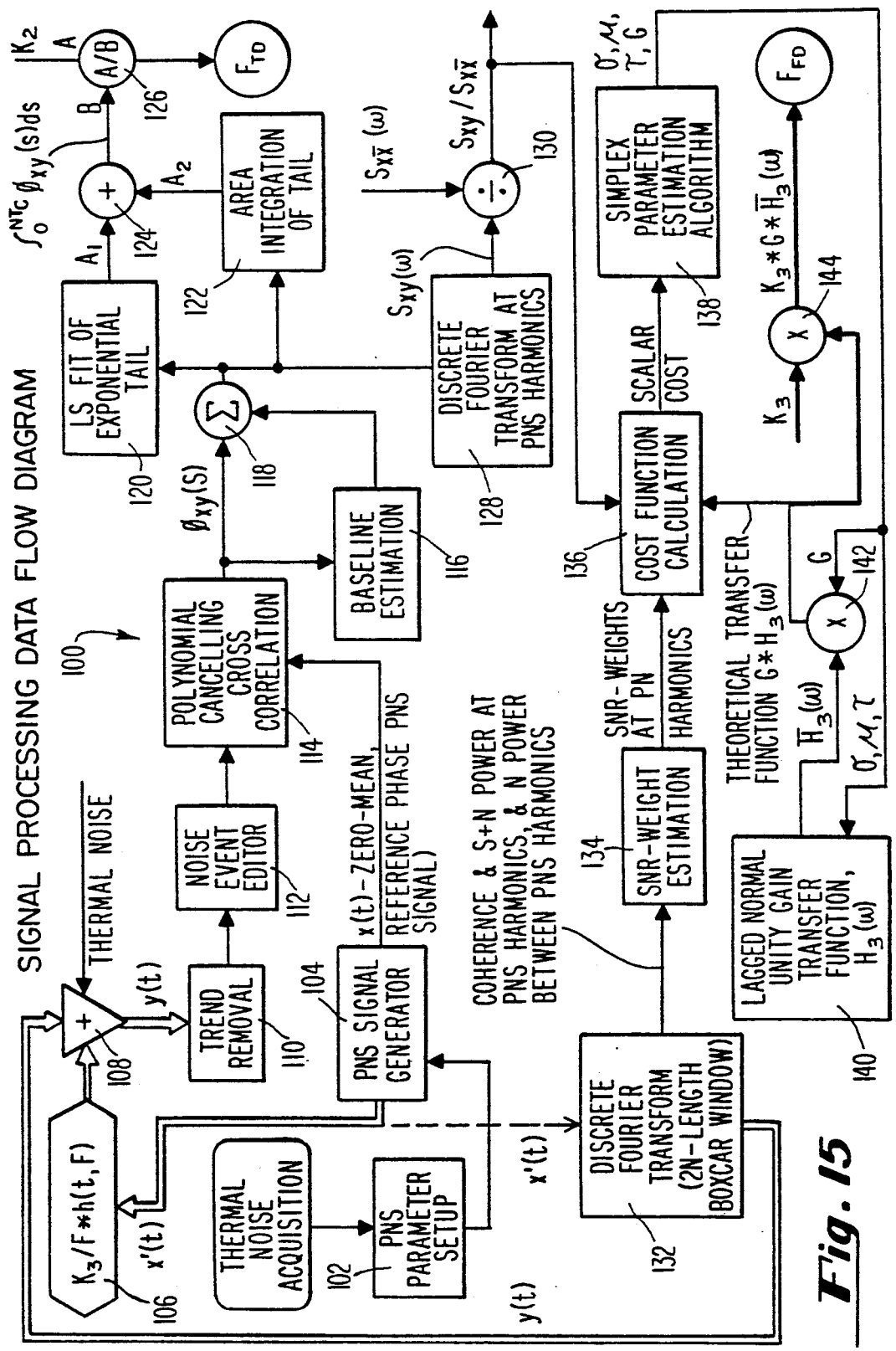

METHOD AND APPARATUS FOR CONTINUOUSLY MEASURING VOLUMETRIC FLOW

CROSS REFERENCE TO RELATED PATENT

The present invention is related to U.S. Pat. No. 4,507,974 to Yelderman, which is incorporated herein by reference in its entirety.

BACKGROUND OF THE INVENTION

1. Field of the Invention

The present invention relates to volumetric flow measurements and more particularly to in vivo blood flow measurements of cardiac output.

2. Description of the Prior Art

Blood flow measurement is an important diagnostic technique used in various medical applications. A prime application is in the diagnostic analysis and treatment of heart conditions, where accurate volumetric blood measurement can be extremely useful, particularly since the physical dimensions of the vessels containing the moving blood cannot be reliably measured. Another important reason for measuring blood flow over a period of time is to determine the effect of medication on cardiac output.

Because of the importance of measuring blood flow in humans, much attention and effort has been devoted to developing a reliable blood flow measurement technique. A primary desire is to determine the blood flow exiting from the heart. It is well known to those of ordinary skill in the art that several physiological factors have been particularly difficult to overcome. For example, because the flow distribution of blood from the heart is non-stationary and dynamic, measuring blood flow at a peripheral artery does not provide an accurate estimate by extrapolation of primary heart blood flow. Moreover, measuring blood flow at the heart implies that the site of the flow measurement is the pulmonary artery or the aortic root, both of which are relatively inaccessible to a measuring device, although the pulmonary artery is more easily accessed at the bedside than the aorta.

Another physiologic factor which has not previously been fully appreciated is that the main pulmonary artery is relatively short and very elastic, lacking rigidity in all directions. In the clinical environment, the cross-sectional area varies significantly from person to person, and even moment to moment in the same person, depending upon blood volume, drugs, posture, disease states, and even blood flow itself. Any measurement technique which requires assumptions about vessel cross-sectional area is therefore likely to fail in a clinical environment. Thus, as used herein, flow is the measurement of mass fluid movement and relates to the volume of fluid moved per unit time. Knowledge of fluid velocity or velocity profiles is not required, nor is information regarding the cross-sectional area of the flow chamber.

Generally, there are three prior art approaches to measuring blood flow in the pulmonary artery. One way, an invasive procedure, is to mount one of several types of transducers on a flow-directed catheter, insert the catheter through a large peripheral vein such as the superior vena cava, and float it into the heart. A comprehensive review of such techniques for using and inserting pulmonary artery catheters has been given by Keefer et al. in Chapter 9 of a text entitled "Monitoring in Anesthesia and Critical Care Medicine," pp. 177–228, and thus will not be described here. Once in the heart, the transducer can measure the flow of the blood passing it. Velocity can be measured using ultrasound Doppler techniques or by estimating the time of flight between two points on the catheter.

An example of the latter type of system for measuring cardiac output is described in U.S. Pat. No. 4,542,748 to Roy. Such time of flight measurements occasionally utilize stochastic or cross-correlation techniques; however, since they do not estimate cross-sectional area, the ultimate blood flow measurement has an inherent error. Ultrasound techniques, on the other hand, may not only measure blood flow by using the Doppler effect, but also may estimate a cross-sectional area by measuring a vessel diameter as in U.S. Pat. No. 4,733,669 to Segal. In particular, Segal discloses a catheter having a mechanism for positioning a Doppler shift transducer carried by a catheter against a side wall of a blood vessel for accurately monitoring blood flow on the right side of the heart. However, the technique disclosed by Segal provides unacceptably inaccurate data since the vessel is not a perfect circle and hence its cross-sectional area cannot reliably be estimated merely by measuring a diameter. Moreover, as explained above, the pulmonary artery is very short and hence small changes in catheter position also add a component to the error in the flow estimate.

A second method of measuring blood flow is to mount an ultrasound transducer on a vehicle which will lie in a structure surrounding the great vessels, such as the esophagus or trachea, measure flow, and estimate vessel cross-section. An example of such a method is disclosed in U.S. Pat. No. 4,722,347 to Abrams et al. Abrams et al. disclose a non-invasive ultrasound apparatus which is inserted into the trachea in proximity to the aorta or pulmonary artery. Ultrasound waves are transmitted toward the path of flow of blood in the artery and reflected waves are received. The average Doppler frequency difference between transmitted and received waves is measured for determining the cross-sectional size of the artery as well as blood flow rate. Abrams et al further disclose in "Transtracheal Doppler: A New Procedure for Continuous Cardiac Output Measurement," Anesthesiology, Vol. 70, No. 1, January, 1989, pp 134–138, that such techniques lead to favorable cardiac output measurements in dogs. However, the methodology used by Abrams et al. dictates that the performance of such devices is still very dependent upon the user's ability to obtain an accurate estimate of the vessel cross-sectional area. Thus, for the reasons pointed out above, these techniques are also unsatisfactory in a clinical environment.

In addition, ultrasound transducers have been placed adjacent to but external to the vascular walls, as in DATASCOPE ™ Company's "ARTERSOUND" ™ system. In this device, two ultrasound transducers are used. One transducer is placed in the esophageal to measure the velocity of the descending aorta, while the other is placed over the sternal notch to measure the aortic root dimensions. Again, as with the devices previously mentioned, the accuracy and precision of such a device is poor. Moreover, significant user experience is needed to obtain the measurements.

Finally, a third method of measuring blood flow is by indicator dilution techniques. Multiple methods of indicator introduction have been taught in the prior art.

One such method is to introduce the indicator proximally according to a predetermined function and to measure the function attenuation distally. For example, waveforms may be introduced either as a step function as disclosed in U.S. Pat. Nos. 4,217,910 and 4,240,441 to Khalil, in "Measurement of Cardiac Output by Thermal-Dilution and Direct Fick Methods in Dogs," J. Appl. Physiol. 21(3):I 1131-35 (1966) by Khalil et al., and in "A Continuous Cardiac Output Computer Based on Thermodilution Principles," Annals of Biomedical Engineering, Vol. 17, pp 61-73, 1989 by Normann et al., or as a series of sine waves as disclosed in U.S. Pat. No. 4,236,527 to Newbower et al. and U.S. Pat. No. 4,380,237 to Newbower, and in "Continuous Thermal Measurement of Cardiac Output," IEEE Trans. on Biomed. Engin., Vol. BME-31, No. 5, May, 1984, pp. 393-400 to Philip et al. The respective references disclose the use of a thermodilution catheter which introduces heat or some other indicator into the blood stream to be propagated downstream and detected. The data collected is then processed to determine blood flow without knowledge of the vessel geometry, for indicator dilution techniques generally do not require knowledge of vessel geometry to determine volumetric flow. However, the techniques of the above-mentioned references are less than satisfactory since in many applications they may require extensive calibration procedures or may be contaminated by background thermal noise.

Thermal noise results from the fact that the temperature of the blood in the superior vena cava is generally higher than that returning from the lower extremities though the inferior vena cava. In other words, the amount and temperatures of such returning blood are not constant and therefore produce variations in pulmonary artery temperature. A primary source of such thermal variation in the temperature of blood within the heart results from respiration. For example, when a breath is taken, the proportion of blood entering the heart from the superior and inferior venae cavae varies, thus varying the temperature of the resulting mixture in the pulmonary artery. Ventilation itself has little or no effect on the temperature of the blood in the pulmonary artery, since the cooling effects of gas exchange occur downstream from that location.

In addition, because blood vessel cross-sectional area is so difficult to reliably estimate, successful clinical methods of measuring blood flow must utilize a technique which does not require knowledge of vessel dimensions. Investigators such as Bassingthwaighte and Rosenkrantz have demonstrated that vascular systems are linear and time invariant, thus permitting classical system identification techniques to be used. Such techniques are described by Bassingthwaighte et al. in "Applications of the Lagged Normal Density Curve as a Model for Arterial Dilution Curves," Circulation Research, Vol. 18, pp. 398-407, April 1966, and by Rosenkrantz et al. in "Pseudorandom Noise and Cross-Correlation in Indicator-Dilution Systems,"Journal of Surgical Research, Vol. 21, pp. 105-11 (1976). The clinical standard, using an indicator dilution method as taught by Stewart in "The Output of the Heart in Dogs," American Journal of Physiology, Vol. 57, pp. 27-50 (1921) is essentially a conversation of mass/heat technique. For example, when using dye, heat, cold, or other indicator, a bolus may be injected into the proximal end of a vessel and its appearance measured at a distal point. Thus, because the indicator is generally conserved, measuring the distal indicator's appearance and knowing the amount injected allows calculation of the true bulk mass blood flow. This technique is further described by Barankay et al. in "Cardiac Output Estimation by a Thermodilution Method Involving Intravascular Heating and Thermistor Recording," Acta Physiologica Academiae Scientiarium Hungericae, Tomus 38(2-3), pp. 167-173 (1970) and by Normann et al. Unfortunately, however, these techniques cannot be safely used with a heat indicator since the application of a "heat bolus" would produce high temperature at the surface of the heater element which may damage blood cells and circulatory connective or muscle tissues. Moreover, such a technique is time consuming and provides only intermittent determinations.

An improvement to the above techniques was provided by U.S. Pat. No. 4,507,974 to the present inventor, which is fully incorporated above by reference. The Yelderman '974 patent incorporates two basic ideas, namely, stochastic system identification and conservation of mass equations. Bassingthwaighte and Rosenkrantz substantiated the system identification principles and Stewart and others verified conservation of mass principles. Yelderman '974 was the first to put the two together by teaching that any indicator may be introduced in the form of any stochastic or spread spectral process. In particular, in that system a catheter mounted heating filament utilizes a stochastic or pseudorandom input to drive the heating element. Such an input causes a continuous low level excitation (nonimpulsive) waveform to be possible which allows for a physiologically safe surface temperature at the heater filament, unlike other systems which require large amounts of peak energy. The vascular system impulse response is then measured downstream and cross-correlated with the input signal. This information is combined with the conservation of heat equation to measure volumetric fluid flow. An advantage of this technique is that the total impulse response function of the vascular tree may be accurately estimated, which is not possible in the prior art system of Newbower, for example, and may be estimated with a low peak power. Knowing the complete response improves performance in the presence of disturbances and eliminates the requirement to calibrate the procedure. Also, the impulse response measurement is combined with a conservation of mass/heat equation that underlies the thermodilution measurement to allow calculation of the true volumetric blood flow. Such measurement is relatively accurate and depends neither upon knowledge nor estimation of vessel cross-sectional area.

However, at present, no thermal filament type based blood flow measuring device has yet been developed or approved for commercial sale in the United States, for when attempts have been made in the past to apply them in clinical settings, they have not proven sufficiently accurate to displace classical injected indicator techniques. Thus, although the technique disclosed by Yelderman provides performance superior to any other known thermal technique in a noisy environment, some improvement is desirable for use in actual clinical settings where the degree of thermal noise is quite high.

Therefore, a long felt need exists to provide an automatic technique of continuously measuring blood flow which does not require knowledge of the vessel cross-section, but which also eliminates or substantially reduces the background noise inherent in the flow system so that the thermodilution flow measurement technique may be adapted to the clinical setting. The present invention has been designed to meet these needs.

SUMMARY OF THE INVENTION

The present invention provides novel methods of determining volumetric blood flow on a substantially continuous basis, even in the noisy environments which are characteristic of clinical settings. It was recognized in the Yelderman '974 patent that the system response of any vessel (as determined by any technique) conformed to a lagged normal model as described by Bassingthwaighte. It was thus found that knowledge of a system's general characteristics, as in the form of a known model, allows curve fitting techniques to be used, which, in turn, provide additional reduction in noise or error. However, the curve fitting technique described in Yelderman '974 used only the exponential portion of the lagged normal model. In particular, the present inventor recognized therein that the theoretical lagged normal distribution equation of Bassingthwaighte for determining blood flow, comprised of Gaussian and exponential decay components, can be fitted against collected blood-flow data of the type collected by the invention of the Yelderman '974 patent to derive estimates of the five variables needed to solve the lagged normal distribution equation for blood flow. The technique of the subject application improves upon that in the Yelderman '974 patent by relying upon the fact that thermal noise, due to its physiologic origins, is not uniformly distributed across the frequency bandwidth of interest. In particular, information regarding the thermal noise is gathered and used to improve the response of the system.

Thus, in accordance with the present invention, at least three, preferably at least seven, and most preferably about fifteen different frequencies may be input to the heat source, either as discrete frequencies or as a pseudorandom ensemble of frequencies. The input is then cross-correlated to its corresponding detected output as taught in Yelderman '974. In addition, a weighting or scalar "cost" function is developed which describes the acceptability or signal/noise ratio for each of the input frequencies (i.e., a frequency weighting function). The scalar cost function is the sum of the squared error between the "measured" and "modeled" transfer functions weighted for each frequency of the input function by the output signal/noise ratio. For example, if the output signal/noise ratio is high, the weighting function approaches one, whereas the weighting function approaches zero when the selected frequency is determined to be severely contaminated by noise. Then, as the determined system response is fitted to the lagged normal model, discrepancies between frequencies are resolved using the weighted cost function, where more weight is given to those frequencies which have the least noise contamination.

The lagged normal curve, as described by Bassingthwaighte and as used in Yelderman '974, has been described in terms of parameters in the time domain. However, as would be apparent to those skilled in the art, any linear system characterized in the time domain can be transformed uniquely into the frequency domain. This transformation of the lagged normal model into the frequency domain is the subject of another aspect of the present application and is described in detail herein. In particular, considerable advantages can be realized by model fitting of the lagged normal to measured cross-correlation data by working in the frequency domain or in the time and frequency domains together. Such advantages are present since a parameter which is difficult to accurately fit in the time domain may be more easily fit in the frequency domain.

Thus, in accordance with the present invention, cross-correlation data is obtained as taught in Yelderman '974. A weighting function is then developed, and a model fit in the frequency domain is performed. Then, from the model fit a determination of the baseline of the lagged normal curve, as well as other parameters, is made. Once the baseline is known, a more accurate flow rate may be determined in accordance with the general techniques taught in Yelderman '974.

In a preferred method, the amplitude and phase of the weighted data is compared in the frequency domain to the theoretical amplitude and phase functions in order to perform a five-variable, complex model function fit, with any inconsistencies being resolved in favor of the weighting function. Using this technique, observed values for the five variables are obtained, from which the blood flow may be readily determined in accordance with the lagged normal distribution equation as herein defined. As a result, the determined flow computed in the time domain corresponds to the zero frequency amplitude of the model functions. In other words, the area under the curve for the time domain system or impulse response is identical to the DC amplitude in the frequency domain.

An alternate method of determining the flow is to estimate the five lagged normal model variables from the weighted data by fitting the derived data to the theoretical lagged normal function in the time domain as described in Yelderman '974. However, this method is generally not as accurate as the aforementioned frequency domain fitting method since available phase and signal/noise ratio information is not utilized.

To further minimize the effects of thermal noise on the system, a preferred method of the present invention relies on providing repetitive trains of input signals having the aforementioned plurality of frequencies. Increasing the observation interval or the length of the input sequences increases the signal/noise ratio since a longer averaging interval is obtained. Comparisons of corresponding observed data for each frequency may then be used to discard aberrant data apparently containing large, transient noise components.

To yet further improve the accuracy of the method of the invention, the power spectrum of the background noise should also be determined and analyzed, most preferably using Fourier analysis techniques, to determine the predominant periodicities of the background noise. The determination of these frequencies allows the code clock duration and frequencies of a pseudorandom binary code, which is used as the primary stochastic input, to be chosen to avoid these periodicities. After this initial determination is made, application of an indicator is made according to the optimized binary code at the input to the vascular system, and the resultant of that input is measured at the output or distal end of the vascular system.

Adjustment for relatively slow thermal drift is also made by a "signal cancelling moving average filter" which removes the low frequency interference. Multiple techniques to remove such drift may be used, some straight forward and others more sophisticated. Typically, the output signal measured at a distal end of the vascular system contains not only the signal of interest but significant low frequency noise or baseline drift which, if not corrected, distorts subsequent processing and leads to errors in the flow estimate. Since the amount of indicator (e.g., heat) input per period of the pseudorandom sequence is constant, any deviation of the output (e.g., temperature) when averaged over an equivalent period can be identified as due to the baseline drift.

To correct such drift, one of several techniques, but preferably two complimentary techniques, may be used. The first preferred technique uses a "moving average filter" which time averages its input over the pseudorandom sequence length and then subtracts its output from a delayed version of the original output signal, point by point. The second preferred technique is to use a "zero-mean reference phase" pseudorandom binary sequence to remove the drift via "polynomial cancelling" cross-correlation formulas. The cross-correlation may be performed using a multiple period Fast Fourier Transform (FFT) algorithm between the input sequence or source, and the resultant distal end measurements. The result is the impulse response of the vascular system. With knowledge of the amount of indicator supplied at the input and using a conservation of mass/indicator equation as taught by Yelderman in U.S. Pat. No. 4,507,974, exact calculation of the volumetric blood flow may be computed.

Previously, the estimation of the impulse response in a noisy environment has been problematical since the noise is uncorrelated with the input source or binary sequence. When the noise is truly uncorrelated and the averaging procedures are of long enough duration, the previous system of Yelderman, for example, allowed a significant amount of the interfering noise to be averaged out. However, if the characteristics of the background or interfering thermal noise are given consideration, as taught by the present invention, significant additional improvements in the performance of such systems can be achieved.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which:

FIGS. 10(a) and 10(b) illustrate a powerful thermal noise event elimination function whereby detected noise levels exceeding the RMS value of the detected thermal temperature waveform are eliminated from the detected temperature data to reduce the effects of coughing, arm and head movement and the like.

FIGS. 13(a) and 13(b) respectively illustrate the amplitude and phase of the cross-spectral density $S_{xy}(\omega)$.

FIGS. 14(a) and 14(b) respectively illustrate the amplitudes of the output power spectrum, $S_{xy}(\omega)$ and the coherence function at each PNS signal harmonic frequency for a spontaneously breathing patient.

FIG. 15 is a block diagram of a data processing system for performing the flow measurement calculations in accordance with the invention.

DETAILED DESCRIPTION OF THE PREFERRED EMBODIMENTS

Figure 1:
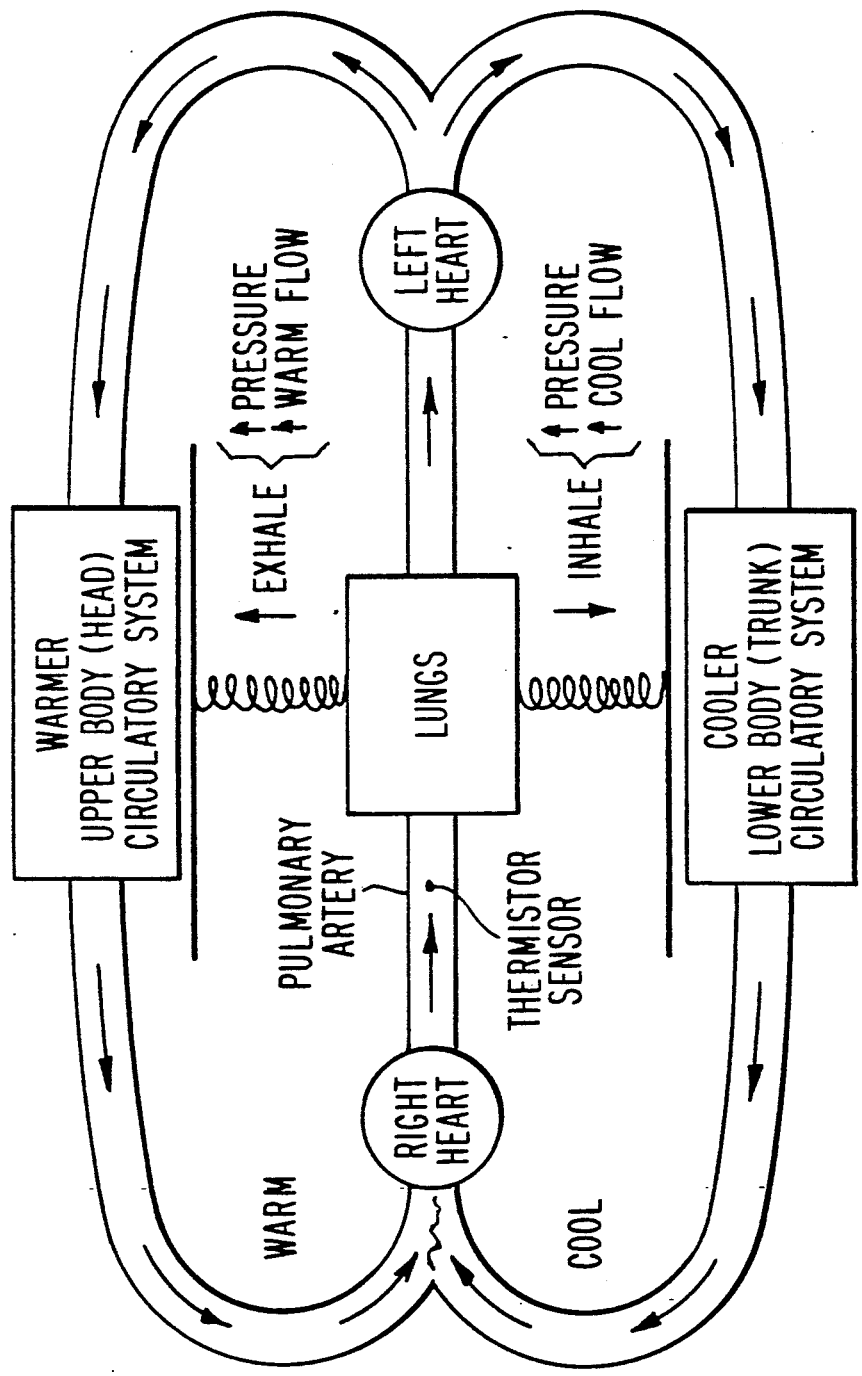
FIG. 1 is a simplified diagram of the circulatory system for illustrating the modulation of blood temperature in the pulmonary artery as a result of breathing.

The process and theory of operation of the present invention and then a particular exemplary embodiment will be described with reference to the attached drawing figures. Like references will correspond to similar features throughout the drawing figures.

The present invention is an extension or enhancement of the Yelderman '947 patent. The Yelderman '947 patent relates to an invention that makes it possible to use physiologically safe heat signals to continuously measure cardiac output, e.g., automatic periodic measurement. The techniques herein disclosed are based on such techniques and make it possible to obtain the desired measurement performance levels (accuracy, response time) given the severe thermal noise environments that accompany many human patients for any input source. Although the invention will be described with reference to thermodilution measurements using a catheter, those skilled in the art will appreciate that the same techniques may be used for other indicators such as radioactive isotopes, dyes or cold. In addition, other intrusive and nonintrusive techniques may also be used for measuring the indicator flow rate in accordance with the invention. All such measurement techniques are intended to be within the scope of the invention as indicated by the appended claims.

PSEUDORANDOM NOISE SEQUENCE PARAMETER SETUP

In the clinical environment, background thermal noise is generally not purely random or purely white noise as assumed in the Yelderman '947 patent, but has a significant amount of the noise power isolated at several frequencies. It has long been recognized that the source of this noise is a result of patient ventilation and therefore the interfering thermal noise is periodic at the fundamental and harmonics of the ventilator frequency for a patient breathing with the aid of a ventilator. Because a significant portion of the interfering power is contained within these frequencies, a procedure which either removes these interfering frequencies specifically or facilitates a stochastic process to operate at different frequencies will exhibit an improvement in performance. As used herein, improvement in performance is measured either by shortened convergence time, with a consequently improved response time, or by improved accuracy, as manifested by an improved signal to noise ratio.

By definition, a stochastic process as taught in Yelderman '974 supplies properly conditioned "white" noise or a pseudorandom binary maximum length sequence as an input signal. As a rule, the "white" noise is continuous over the pass band of the system being tested or identified. In the case of a pseudorandom binary maximum length sequence, on the other hand, multiple frequencies are supplied over the pass band which are discrete and equally spaced over the pass band. The cross-correlation technique in essence selects out these frequencies and rejects all others. However, if the background thermal noise has periodic frequencies which are approximately the same as one of the frequencies of the binary sequence, the cross correlator is unable to differentiate the pseudorandom binary code from the signal. The interfering frequency is then allowed to pass and become incorporated into the final results. For this reason, increased averaging times as in Yelderman '947 will not remove the noise. However, if the background noise spectra is examined before the stochastic process is started or during the stochastic process, the code clock duration, and consequently the frequencies, can be selected to avoid the predominant periodicities of the background thermal noise. Such is one improvement of the present invention over the Yelderman '974 system. This technique will now be described.

The source of this thermal noise can be understood from the simplified circulatory diagram in FIG. 1. As shown, the blood returning from the upper body is warmer than that from the lower body, and as a result, the temperature of the blood leaving the right side of the heart depends on the relative mix of the two blood return sources. This mixing ratio is modulated by the respiratory induced intra-thoracic pressure and the relative blood pressure of the two venous return paths. Breathing and changes in body position modulate the vascular intra-thoracic pressure of the blood in the pulmonary artery by means of changing the pressure head driving the "hot and cold" blood into the right side of the heart. For example, inhaling lowers the intra-thoracic pressure which decreases the ratio of "hot" to "cold" blood which, in turn, results in a decrease in blood temperature leaving the right side of the heart.

Figure 2:
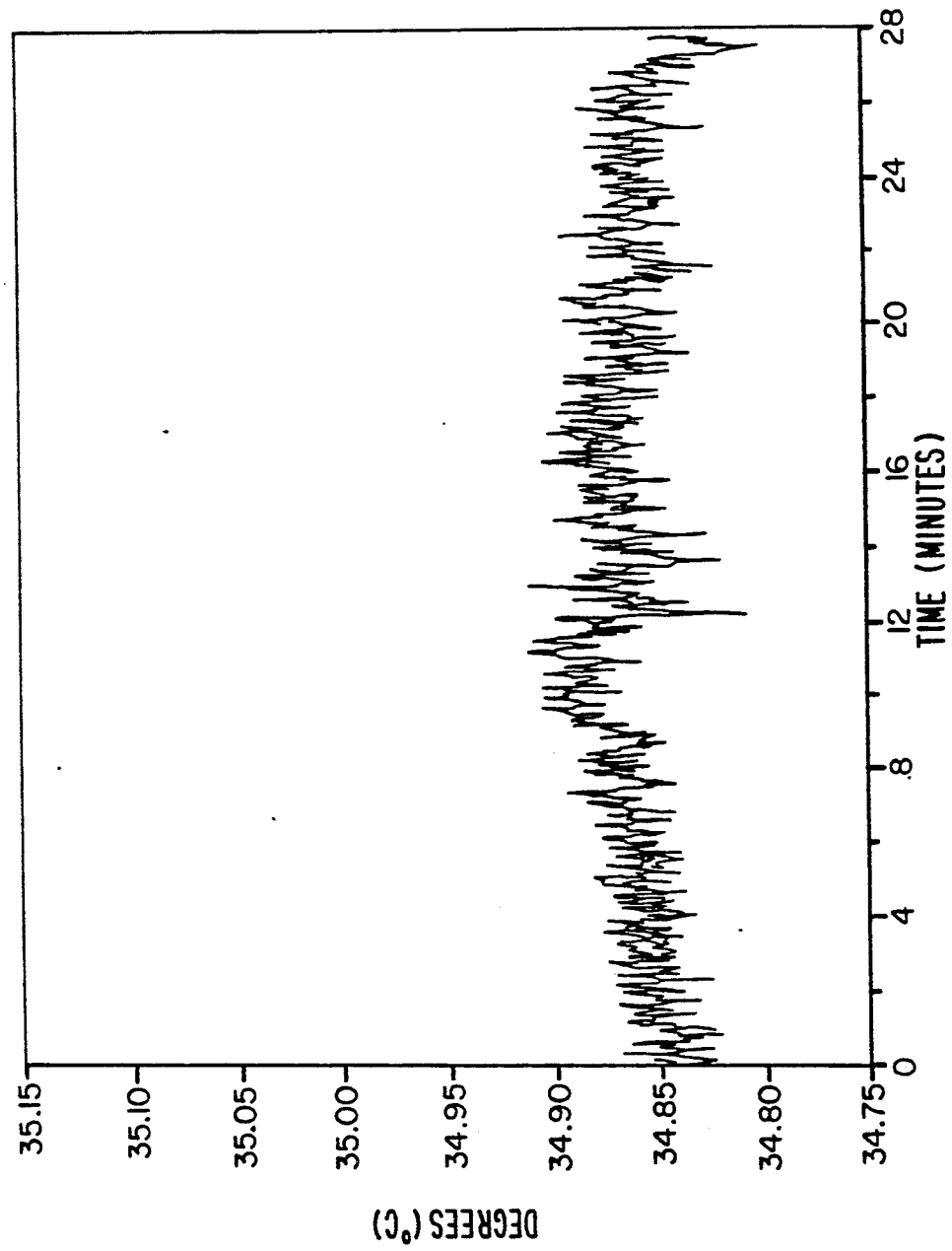
FIG. 2 illustrates changes in background thermal noise with respect to time for a patient connected to a ventilator.
Figure 3:
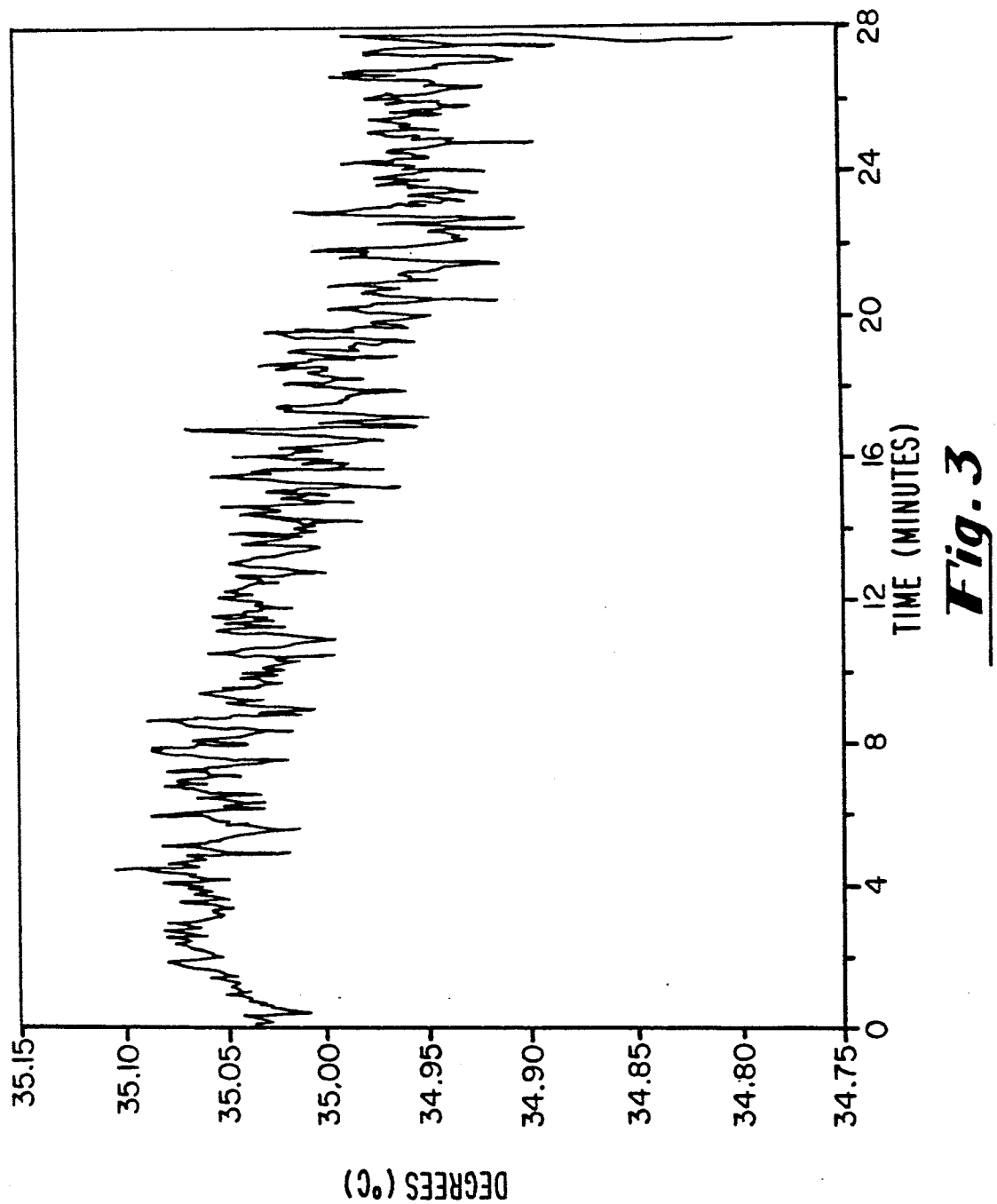
FIG. 3 illustrates changes in background thermal noise with respect to time for a spontaneously breathing patient.
Figure 4:
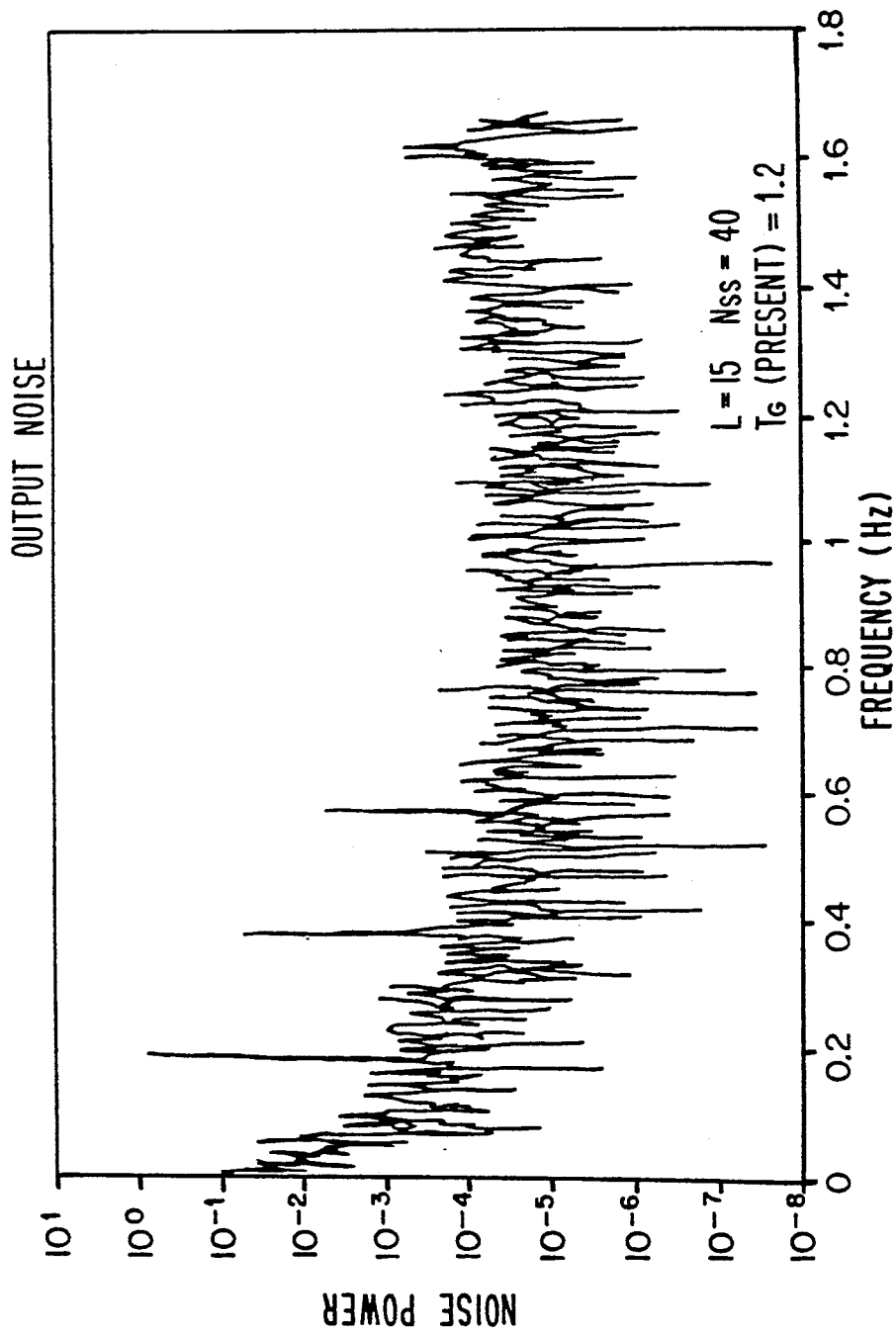
FIG. 4 illustrates the power spectra for the background thermal noise of FIG. 2.
Figure 5:
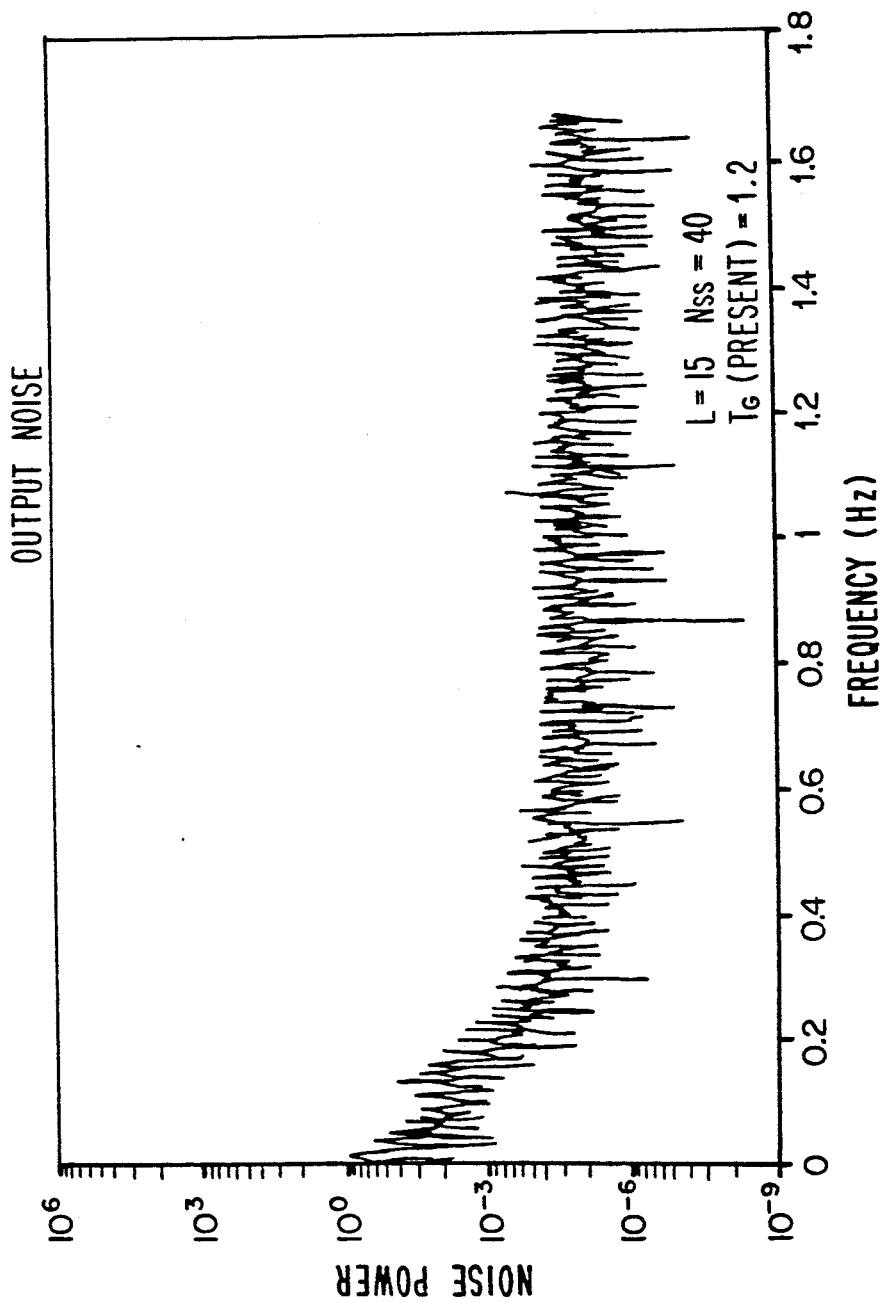
FIG. 5 illustrates the power spectra for the background thermal noise of FIG. 3.
Figure 6A:
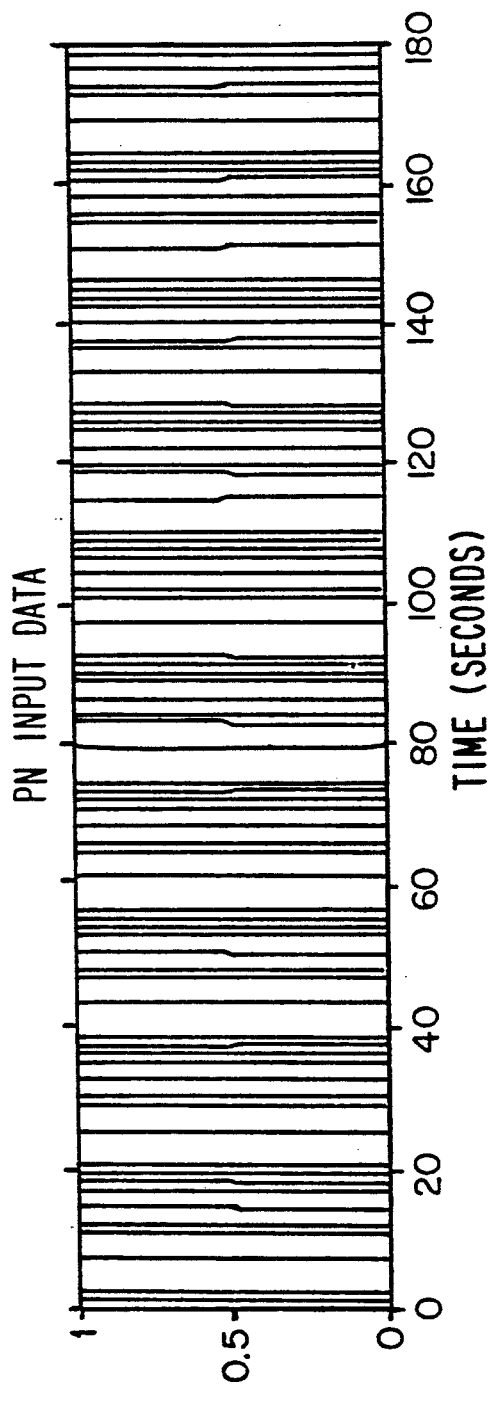
FIG. 6(a) illustrates the time series of a typical pseudorandom input data sequence.
Figure 6B:
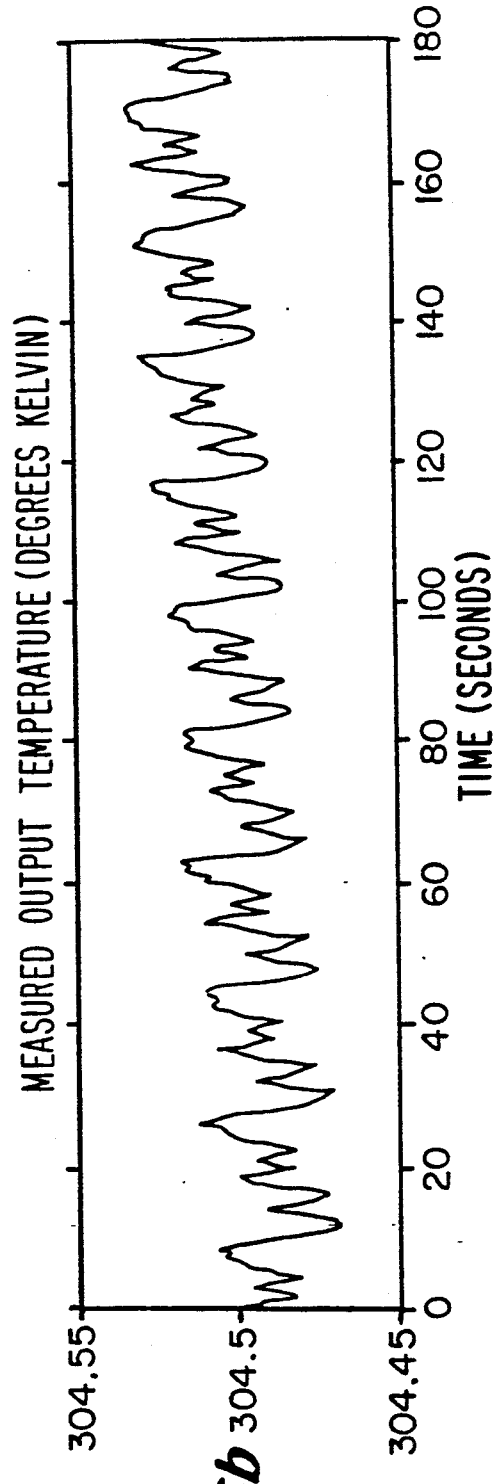
FIG. 6(b) illustrates the measured temperature output in °K for the input data sequence of FIG. 6(a).
Figure 7:
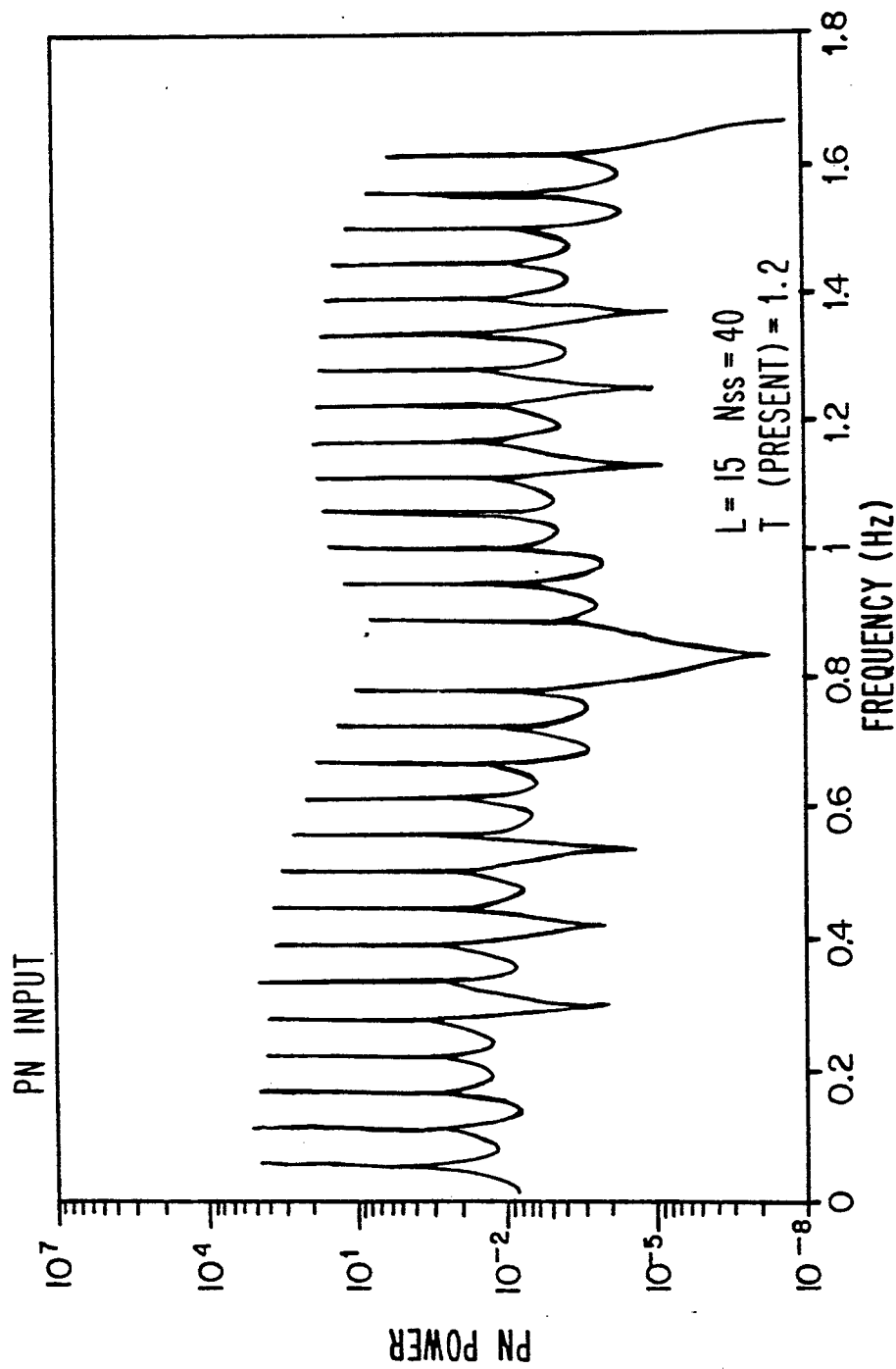
FIG. 7 illustrates the power spectra for the input signal of FIG. 6(a).

Since respiration is a primary modulator of the pulmonary artery blood temperature, there are two classes of noise environments in operating room/intensive care patients: (1) ventilator dependent patients (patients which have a tube inserted into their bronchial passage and are receiving air from a ventilation device) and (2) spontaneously breathing patients. FIGS. 2 and 3 ar typical time records of the background thermal noise for ventilator and spontaneously breathing patients, respectively. The corresponding power spectra are shown in FIGS. 4 and 5, respectively. For comparison, the time series and power spectra of a typical input pseudorandom noise sequence (PNS) of length 15 are shown in FIGS. 6(a) and 7, respectively, and the corresponding measured output temperature is shown with respect to time in FIG. 6(b). As will be appreciated, the spontaneously breathing noise is characteristically non-stationary low frequency noise whereas the ventilator noise is higher frequency narrow band tonal interference having 2 or 3 harmonics (FIG. 4).

Although there are several ways to accomplish the identification of the interfering ventilator periodic frequencies, the preferred method of the invention is to utilize a Fast Fourier Transform (FFT) or similar analytical tool. For example, in FIGS. 2 and 3 sample characteristic tracings of background thermal noise are shown, while FIGS. 4 and 5 represent the corresponding power density spectrum or Fast Fourier Transform of the tracings of FIGS. 2 and 3. As is apparent from FIG. 4, over one third of the total thermal noise power is isolated at the ventilator fundamental frequency of 0.194 Hz and the first harmonic 0.387 Hz. The selection of the proper clock state for input frequencies using these data is illustrated with reference to Table 1 for a ventilator rate of approximately 11.62.

TABLE 1

| respiratory rate | 11.623529 |
|---|---|
| ventilator fundamental frequency (in Hz) | 0.194 |
| 1st harmonic frequency (in Hz) | 0.387 |
| clock duration (in seconds) | 2.23 |
| No. of nonzero code states | 15 |

| Code Harmonic | Code Frequency | Intermediate Frequency |
|---|---|---|
| 0 | 0.000 | 0.015 |
| 1 | 0.030 | 0.045 |
| 2 | 0.060 | 0.075 |
| 3 | 0.090 | 0.105 |
| 4 | 0.120 | 0.135 |
| 5 | 0.149 | 0.164 |
| 6 | 0.179 | 0.194 |
| 7 | 0.209 | 0.224 |
| 8 | 0.239 | 0.254 |
| 9 | 0.269 | 0.284 |
| 10 | 0.299 | 0.314 |
| 11 | 0.329 | 0.344 |
| 12 | 0.359 | 0.374 |
| 13 | 0.389 | 0.404 |
| 14 | 0.419 | 0.433 |
| 15 | 0.448 | |

As shown in Table 1, for a sample binary maximum length code sequence having 15 states, a specific code frequency exists for each code length which is comprised of the code number divided by the clock duration. In this example, the clock duration is 2.23 seconds. In Table 1, the code frequencies (in Hz) are tabulated, and for each two respective code frequencies, an intermediate frequency is determined that is equally spaced between them. For example, for the first and second code frequencies, 0.030 and 0.060 Hz, the intermediate frequency is 0.045 Hz.

In order to eliminate interference from periodic background frequencies the clock time must be chosen so that one of the intermediate frequencies is close to the fundamental ventilator frequency. In the example provided a clock duration of 2.23 seconds yields an intermediate frequency of 0.194 Hz which is intermediate code state 6 and code state 7 as shown in Table 1. This is the same frequency as the fundamental ventilator frequency of 0.194 Hz. However, for the example given in Table 1, the first harmonic of 0.387 Hz is nearly the same as the code state 13 (0.389 Hz). Therefore, to substantially eliminate interfering background noise a better strategy may be to select a clock time slightly different from 2.23 seconds so that this first harmonic frequency is also avoided.

In practice, the input signal must be chosen to avoid the interfering background noise frequencies while also providing sufficient broad band excitation to drive the heater element. Although other input signals may be used, a maximum length binary pseudorandom noise sequence (PNS) of length 15 is selected in a preferred embodiment due to its relative simplicity. This length provides a good match of the state clock time to the thermistor time constant given the 20 to 30 second duration of the thermodilution impulse response. On the other hand, any input signal may be provided and the interfering background noise frequencies determined during the convergence of the readings in response to the input signal. Hence, the system may adjust to make the best readings from the input signal provided by adjusting the input signal to avoid interfering background noise frequencies or simply ignoring the data at the frequencies contaminated by background noise.

For ventilator patients, the duration, Tc, of each state in the sequence, where the time duration of the sequence is L*Tc (L=sequence length=15), can be chosen such that a tonal interference is placed halfway between two harmonics of the PNS signal as described above. More particularly, by measuring the spectrum of the input thermal noise, a duration Tc may be provided which minimizes the effects of the fundamental and first harmonic frequencies of the ventilator noise. For spontaneously breathing patients, on the other hand, it is possible to improve the thermal noise elimination by using shorter Tc durations since this puts the signal energy at higher frequencies. A trade-off is realized between the low frequency thermal noise below 0.5 Hz and the attenuation due to "low pass" characteristics of the thermistor above 1 Hz. Thus, the proper setting of duration Tc for spontaneously breathing patients is left to one of ordinary skill in the art in accordance with the teachings herein.

Consequently, in accordance with the above techniques the present invention selects clock durations and frequencies for use with stochastic flow measurement systems so that the effect of periodic background noise, such as that caused by ventilation, is substantially reduced. The predetermination of the fundamental and harmonic frequencies which predominate the background noise can be accomplished by numerous methods and using apparatus well known to those of ordinary skill and thus will not be discussed here. Moreover, since it should be readily appreciated by one of ordinary skill in the art how the removal of those frequencies interfering with the determination of volumetric flow will substantially improve the performance of volumetric flow measurement systems, further details will not be provided here.

LOW FREQUENCY DRIFT REMOVAL

Background thermal noise having a lower frequency than the lowest harmonic of the PNS signal (the fundamental frequency which has one cycle per sequence length) is referred to as the low frequency drift or trend. If the detected signal has a drift, error will be introduced into the cross-correlation function and the system impulse response. As noted by Yelderman in the '974 patent, it is normally necessary to obtain a baseline for the dispersion function, and to do so, the cross-correlation function is offset to remove bias. In that system, a response function normalizer is provided which receives as input the output of the cross-correlator over one or more runs and processes this data to provide an output having a baseline offset factor B. The response function normalizer computes B by assuming first that the response function represents a single decaying exponential process and then employing a least means squared error (LMSE) technique for fitting the post peak portion of the impulse response function to the best exponential curve. The impulse response function best fitting the best-fit exponential curve is used to calculate the baseline value B.

Low frequency drift may be removed by several methods, two of which are described herein, namely, an ordinary polynomial fitting algorithm and a polynomial fitting algorithm in combination with a zero-mean reference pseudorandom binary sequence. The first low frequency drift removal method in accordance with the present invention takes advantage of the fact that regardless of the noise, average supplied signal power over each sequence of the pseudo-random sequence is a constant. In other words, the total energy supplied by the pseudo-random input source and the total detected energy contributed by it are the same for each complete sequence due to the conservation of heat. As a result of this observation, a segmented low frequency drift removal method may be used in accordance with the present invention to basically fit a quadratic curve to several points. These points may be identified as the average power computed from several adjacent PN sequences at a time. In a preferred embodiment, however, three points are used, and the portion of the fitted curve which is associated with the center sequence is then subtracted from the sequence to provide "zero mean" data. The resulting "segment window" is then moved down one sequence and the curve fitting procedure repeated. Such a procedure is advantageous in that it can quickly follow the random large deflections of the temperature drift that are associated with moving patients or patients being given intravenous injections.

By contrast, the second method makes use of the fact that the pseudorandom binary sequence by its nature can aggravate or diminish the effect of low frequency drift by the sequence order and the starting point. In fact, by properly selecting the appropriate PNS and the proper starting point of the sequence, the effect of drift can not only be reduced, but also entirely eliminated.

Figure 8A:
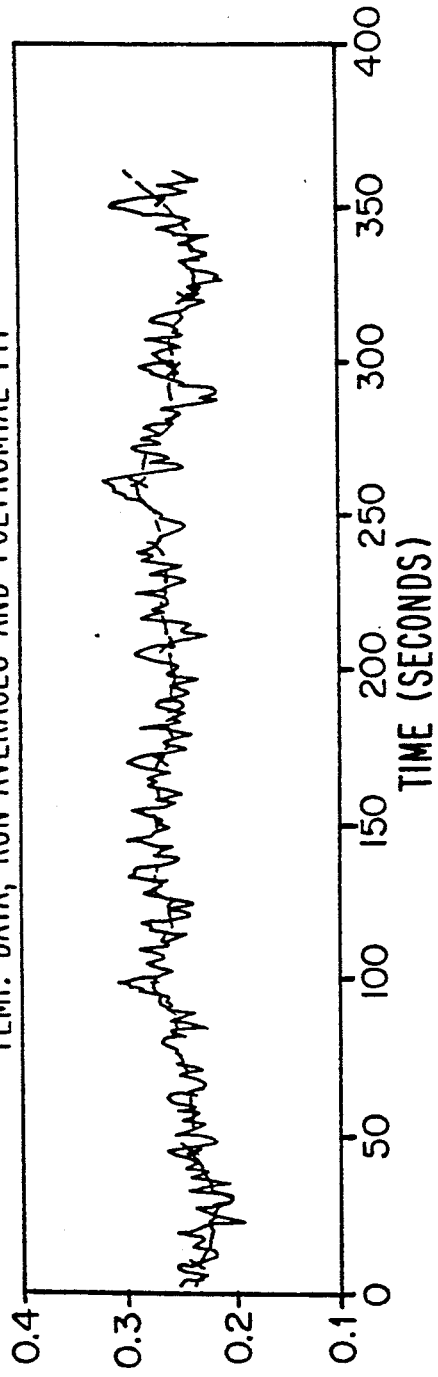
FIGS. 8(a) and 8(b) respectively illustrate variations in the temperature baseline of a patient and the result of removal of the baseline drift.
Figure 8B:
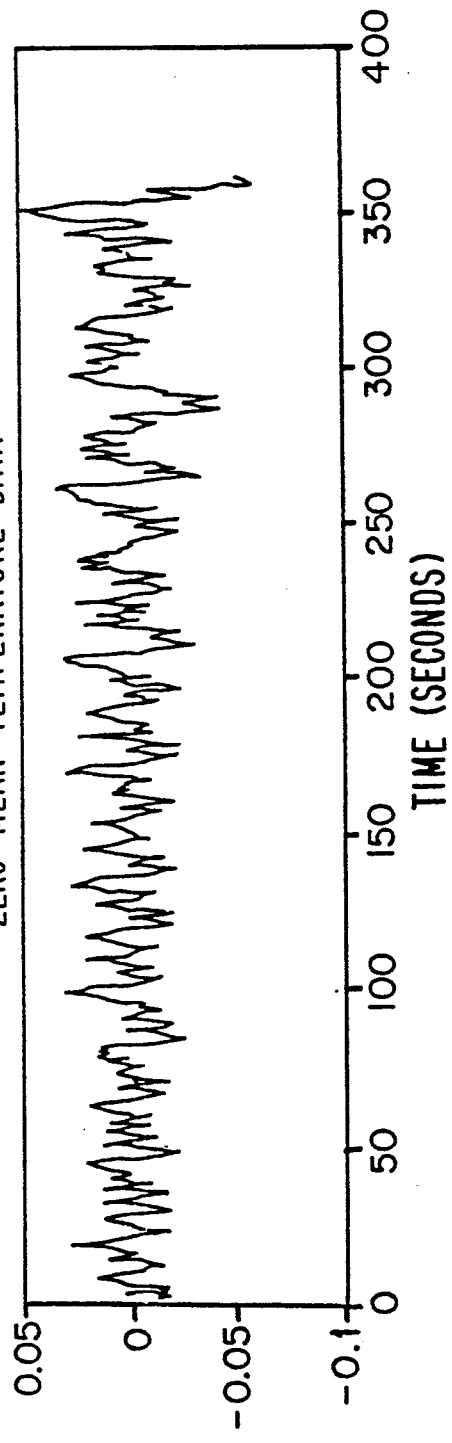

FIG. 8 shows the effects of the low frequency drift or trend removal method of the invention whereby the drifting spontaneous breathing noise shown in FIG. 8(a) is corrected (FIG. 8(b)) using the "segment window" method described above. As shown in FIG. 8(b), the amplitude of the corrected temperature data is greatest at the points where maximum drift from the quadratic curve fitted to the three adjacent points occurs. In any event, this "segment window" method provides results equal to or better than that of the standard polynomial fit trend removal method of the type referenced above, and it has demonstrated a marked improvement in the flow estimation performance.

THERMAL NOISE EVENT EDITING

The occurrence of powerful thermal noise events having durations of 1 to 30 seconds may cause serious errors in the cross-correlated output data. Powerful thermal noise events of such a type are most common for spontaneously breathing patients, but such thermal noise events may also be observed in ventilator patients. A powerful thermal noise event as herein referenced may be caused by intravenous injections or anything that modulates the relative pressure heads of the "hot and cold" venous returns paths (FIG. 1). For example, as noted above, such thermal noise events may include coughing, arm movement, head movement and the like. As a result, means have also been provided in accordance with this invention to eliminate the effects of such powerful thermal noise events by automatically removing those data segments corresponding to thermal noise events from the temperature data and thereby preventing the contamination of the PNS-temperature cross-correlation waveform, $\phi_{xy}(s)$, shown in FIG. 9. As is apparent from the following description of FIG. 9, the fidelity of the PNS-temperature cross-correlation waveform $\phi_{xy}(s)$ is critical to the performance of the flow estimation method in accordance with the invention.

Figure 10A:
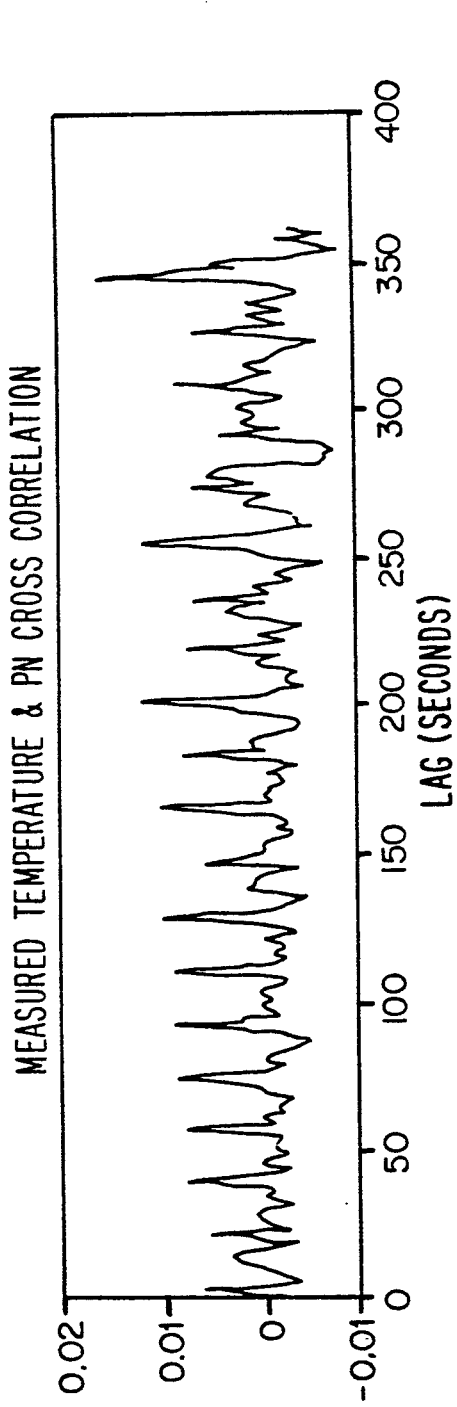
Figure 10B:
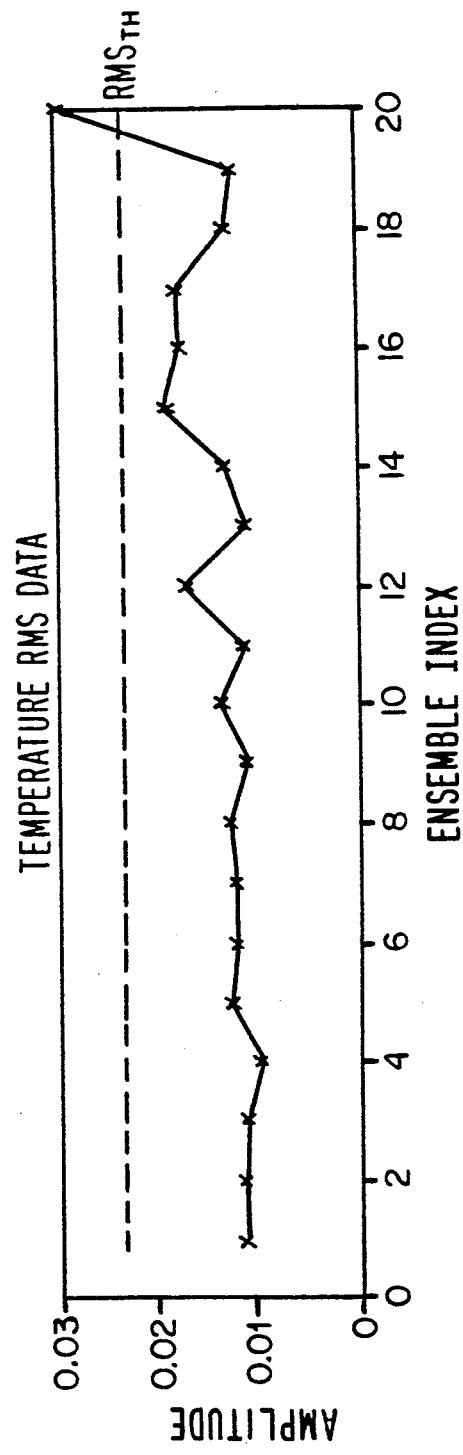

Accordingly, in order to eliminate the effects of powerful thermal noise events of the type described, editing means are provided for removing aberrant data caused by such noise events. Although complex run or ensemble editors may be used for this purpose, a more simple preferred embodiment is described herein whereby the root means square (RMS) value of the temperature waveform is computed for each PNS in the data block used for a flow estimate. Since the signal power due to the input is constant for each PNS, any variability (increase) in the RMS value is a measure of the additive noise level. As a result, the RMS data may be sorted according to amplitude as shown in FIG. 10(a), and a mean and standard deviation of the RMS data may be computed by ignoring the largest percentage (for example, 20 percent or the largest two RMS data values for ten sequences total). Then, by using the calculated mean, $RMS_{mean}$, and the standard deviation, $RMS_\sigma$, a threshold, $RMS_{th}$, may be set according to the following equation:

$$RMS_{th} = RMS_{mean} + K \cdot RMS_\sigma,$$

where K is a preset constant (e.g., 2). Then, any of the sequences having RMS values above this threshold (FIG. 10(b)) will be considered to be contaminated by noise events and may thus be excised from the temperature time series used to compute the cross-correlation data $\phi_{xy}(s)$. In other words, when the ensemble index of the amplitude of the RMS data of the PNS cross-correlation output of the type shown in FIG. 10(a) exceeds the calculated RMS threshold shown in FIG. 10(b), it is determined that a noise event has occurred so that the corresponding data may be eliminated from the temperature time series and hence removed from the cross-correlation data.

Of course, other similar threshold techniques may be used by one of ordinary skill in the art for noise editing without departing from the scope of the invention as identified by the appended claims.

TIME DOMAIN VOLUMETRIC FLOW ESTIMATION

To further improve the overall volumetric flow measurement performance in noisy environments, in accordance with the invention the cross-correlation data is systematically analyzed using a mathematically accurate model of the thermodilution system. In other words, the lagged normal density function disclosed by Bassingthwaighte et al. in "Applications of the Lagged Normal Density Curve as a Model for Arterial Dilution Curves," Circulation Research, Vol. 18, pp. 398–407 (1966), has been mathematically expressed in accordance with a preferred embodiment of the invention in a closed form impulse response and frequency transfer function whereby a pseudorandom sequence (i.e., stochastic signal) is provided as an input and a low-pass filter is provided for the output transducer (i.e., thermistor). The mathematical models of the present invention are used to extract the physically meaningful parameters of the system such as $\tau$, $\sigma$, $\mu$, gain G, and baseline offset, which, in turn, provide clinically meaningful parameters and a means to calculate volumetric blood flow. The definitions of these parameters now will be described with reference to FIGS. 9 and 11 although the lagged normal equation will be described in further detail below with respect to the frequency domain flow estimation method.

Figure 9:
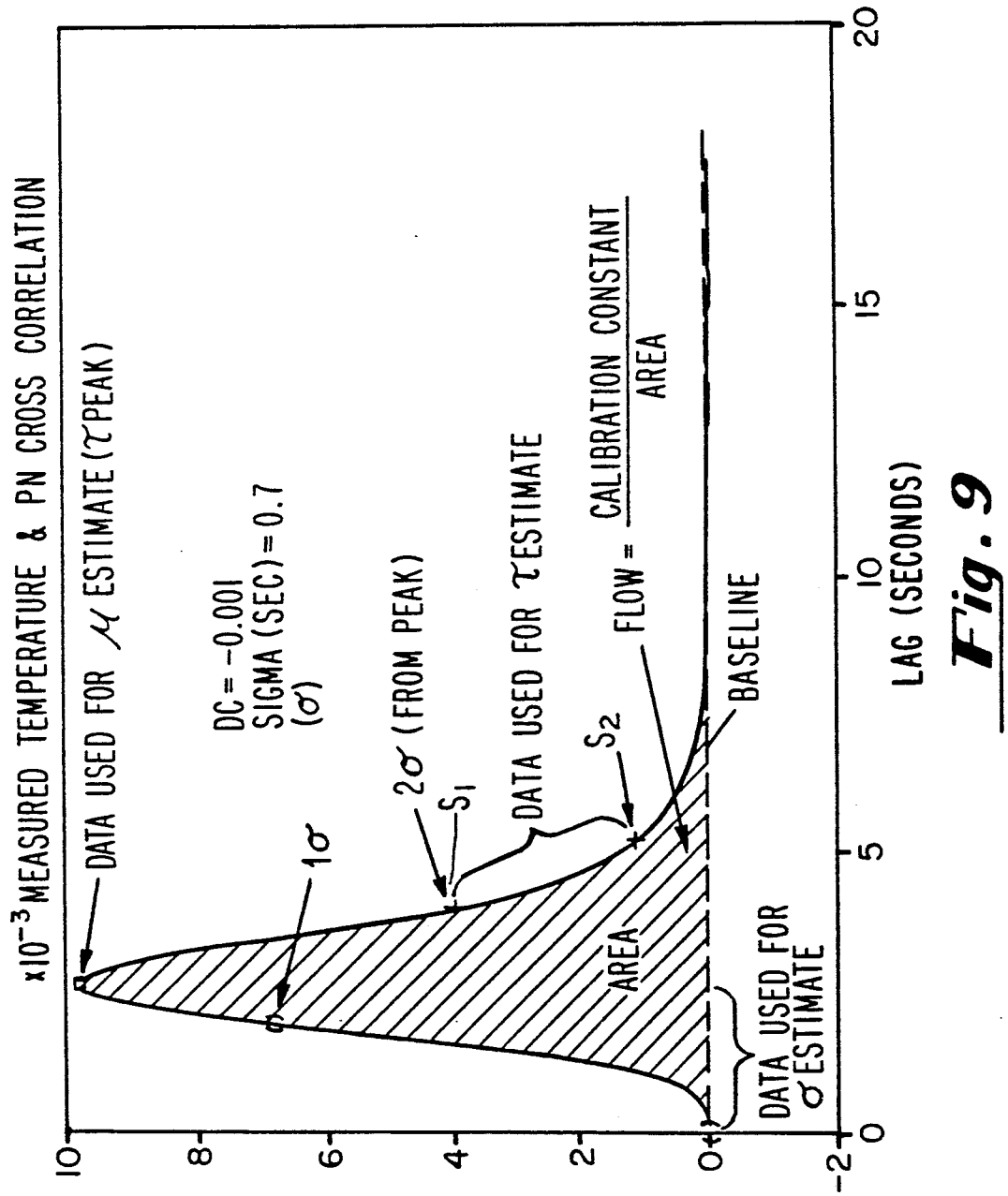
FIG. 9 illustrates the measured temperature and pseudorandom number cross-correlation curve for use in determining the parameters of the lagged normal equation.

The algorithm for determining the lagged normal model parameters in the time domain is as follows. The standard deviation parameter, $\sigma$, is estimated by computing a "cumulative distribution function" (CDF) derived from the rising portion of the measured temperature and pseudorandom number cross-correlation $\phi_{xy}(s)$ curve and finding the lag index whose CDF is closest to about 31.7% as shown in FIG. 9. The $\sigma$ value is plotted as the middle circle in FIG. 9. The exponential decay parameter, $\tau$, on the other hand, is estimated from the falling portion of the cross-correlation data curve starting at a lag point which is twice the value of $\sigma$ after the peak as shown in FIG. 9. The mean transit time parameter, $\overline{X}$ (where $\overline{X} = \mu + \tau$), of the lagged normal function is estimated as the lag associated with the peak of the cross-correlation data as shown in FIG. 9. The values for $\sigma$, $\tau$ and $\mu$ may thus be used as first approximations for the frequency domain model fitting algorithm to be described below. The method used to determine the baseline is to first circularly rotate the $\phi_{xy}(s)$ data to the right by one Tc period. This insures that the rising portion of the $\phi_{xy}(s)$ curve is to the right of the origin, which is necessary since $\phi_{xy}(s)$ is equivalent to the convolution of a triangle function at the origin and the system's impulse response. The minimum value is the first two Tc periods from the origin and is used as the baseline, which is then subtracted from the $\phi_{xy}(s)$ curve to provide $\phi_{xy}(s)'$.

Figure 12:
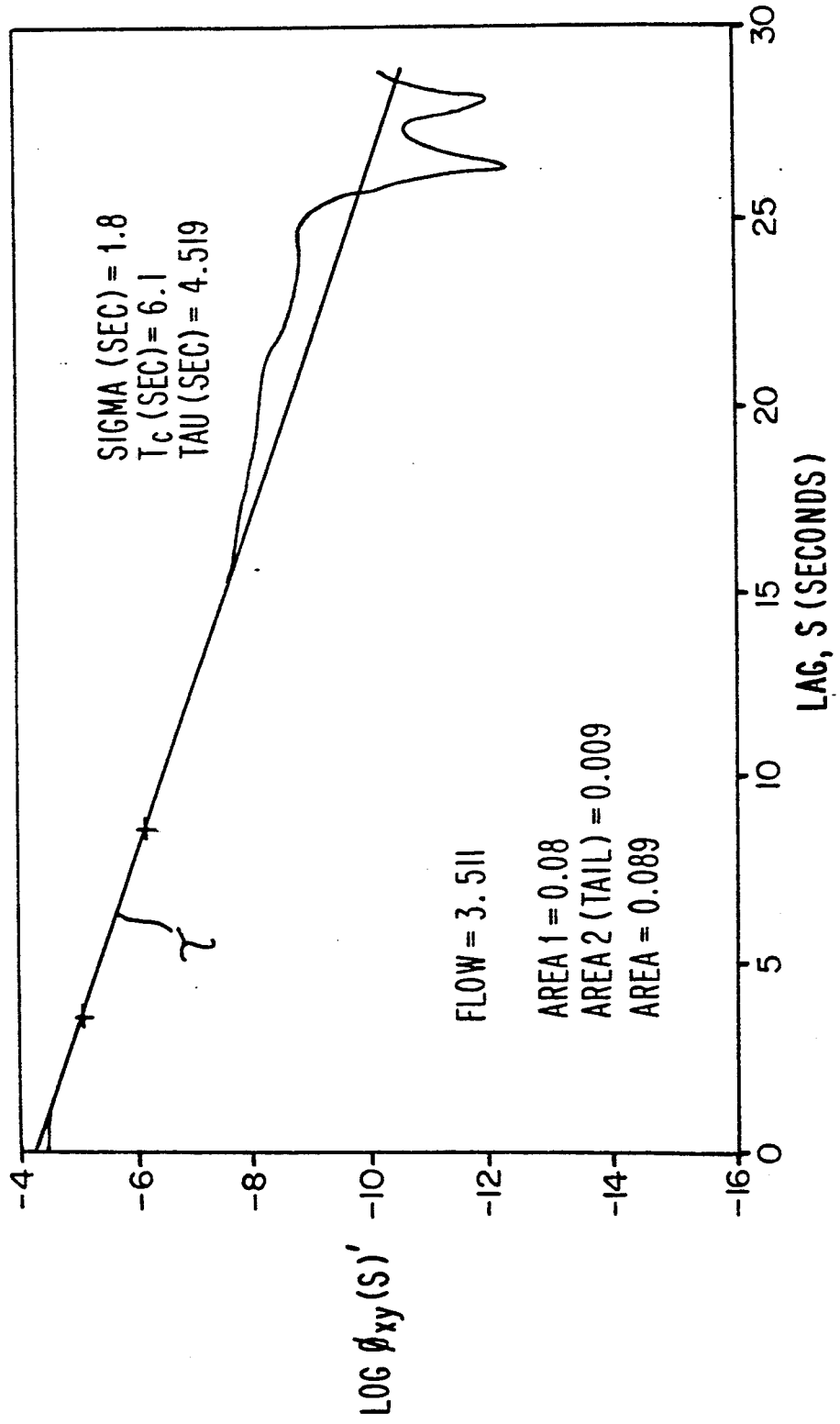
FIG. 12 illustrates the log of the descending portion of the cross-correlation $\phi_{xy}(s)'$ curve with respect to s as used in calculating the exponential decay constant $\tau$ of the tail of the $\phi_{xy}(s)'$ curve.

The rising portion of the $\phi_{xy}(s)'$ data is next used to generate an ascending cumulative function from which an estimate of the effective standard deviation, $\sigma$, is computed, where it is assumed that the rising portion was the left hand side (LHS) of a Gaussian curve. The descending portion of the $\phi_{xy}(s)'$ data is then plotted semilogarithmically ($\log(\phi_{xy}(s)')$ vs. s) as shown in FIG. 12. The $\log(\phi_{xy}(s)')$ data between $s_1 = \tau_{peak} + 2 \cdot Tc$ and $s_2 = s_1 + 2 \cdot Tc$ is then fit to a straight line to determine the exponential decay constant $\tau$. The area under the $\phi_{xy}(s)'$ curve is then computed as:

$$\text{Area} = \sum_{s_0}^{s_2} \phi_{xy}(s)' + \tau \cdot \phi_{xy}(s_2).$$

As will be described in more detail below, this area is divided into a constant $k_2$ to provide the flow estimate $F_{td}$ in the time domain. The above estimate of the area past $s_2$ (second term) provides considerable immunity to errors due to the baseline noise.

Figure 11A:
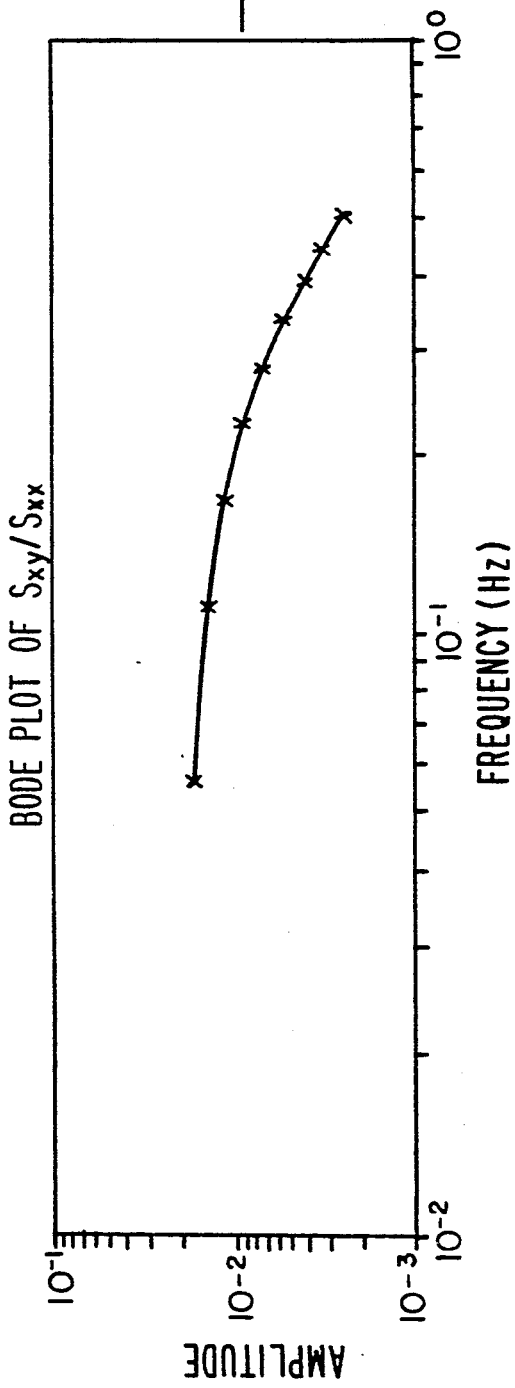
FIGS. 11(a) and 11(b) respectively illustrate the frequency domain transfer function amplitude and phase for use in refining the estimates of the parameters of the lagged normal equation.
Figure 11B:
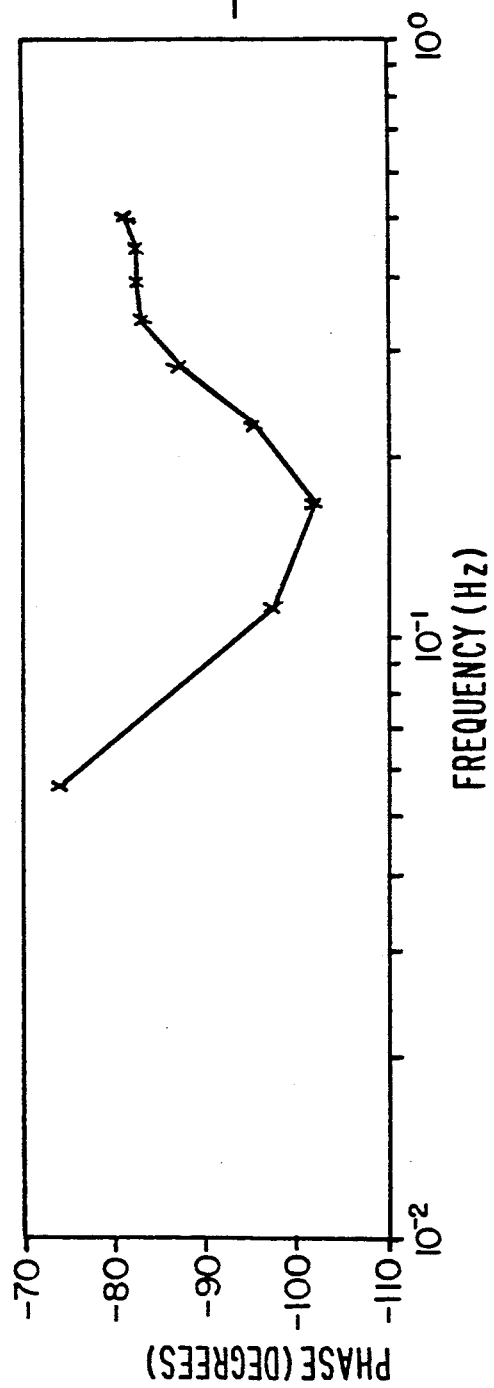

The $\sigma, \mu$ and $\tau$ parameter estimates may be refined by fitting the expression of transfer function phase to the phase data as in FIG. 11(b). In addition, the expression for the transfer function amplitude may be used to extract the DC current intercept (and hence DC offset $\mu$)

from the amplitude data as shown in FIG. 11(a). This parameter is then divided into a scalar calibration constant to estimate the flow by dividing by the area under the curve as shown in FIG. 9. Finally, the gain G is a scaling factor used since the area under the curve is generally not exactly equal to 1, although such is assumed in the mathematical representation of $\phi_{xy}(s)$.

As developed in the Yelderman '974 patent, the area under the $\phi_{xy}(s)$ curve is inversely proportional to flow. Accordingly, the time domain volumetric flow estimate in liters per minute is defined as:

$$F = \frac{k_2}{\int_0^{NTc} \phi_{xy}(s)ds}, \quad (1)$$

where the constant $k_2$ is determined from the conservation of mass equation in conjunction with stochastic signal processing techniques as set forth in the Yelderman '974 patent.

Dispersion models are useful for model fitting capabilities since they strengthen signal to noise considerations and hence will be discussed here. Bassingthwaighte sets forth the random dispersion model for arterial dilution curves using the equation for a truncated normal density as:

$$h_1(t) = \frac{1}{\sigma(2\pi)^{\frac{1}{2}}} \cdot e^{-\frac{1}{2}[(t-\mu)/\sigma]^2} \text{ for } t \geq 0 \quad (2)$$

and $$h_1(t) = 0 \text{ for } t < 0.$$

$h_1(t)$ is defined as a frequency function of unit area and represents a symmetric random distribution of the transit times of an indicator about a central time, $\mu$ (seconds), with a standard deviation, $\sigma$. As shown in FIG. 9, the resulting curve is a Gaussian or a normal distribution curve $\phi_{xy}(s)$. A first-order exponential process is also involved to represent the exponential decay of the following portion of the cross-correlation data curve. This is defined as:

$$h_2(t) = \frac{1}{\tau} \cdot e^{-t/\tau} \text{ for } t \geq 0 \quad (3)$$

and $$h_2(t) = 0 \text{ for } t < 0,$$

where $\tau$ is the time constant and $h_2(t)$ has unit area. $\tau$ is defined such that the flow through a hypothetical mixing chamber washes out the indicator (heat) at a rate such that the concentration at the end of an interval of a duration $\tau$ is $1/e(=1/2.718=0.371)$ of its initial value.

The convolution of equations (2) and (3) mathematically represents the sequential or simultaneous effect of one process on the distribution produced by the other and may be described by a differential equation as follows:

$$h_3(t) = \frac{1}{\sigma(2\pi)^{\frac{1}{2}}} \cdot e^{-\frac{1}{2}[(t-tc)/\sigma]^2} - \tau \frac{dh_3(t)}{dt}, \quad (4a)$$

or $$h_3(t) = \int_0^\infty \frac{1}{\sigma(2\pi)^{\frac{1}{2}}} \cdot e^{-\frac{1}{2}[(\lambda-\mu)/\sigma]^2} \cdot \frac{1}{\tau} e^{-(\lambda-t)/\tau} d\lambda, \quad (4b)$$

which also has unit area. The three parameters described above, namely, $\sigma$, $\tau$, and $\mu$, provide a complete description of the curve's shape and position in time. The function $h_3(t)$ defines the parameters of the curve and also describes the indicator time distribution. Hence, the indicator distribution $c(t)$ when scaled by flow and quantity of indicator is equal to the $h_3(t)$ function. In other words:

$$h_3(t) = \frac{F}{q} \cdot c(t), \quad (5)$$

where:
F is the flow (in liters/sec);
q is the quantity of introduced indicator (in mg); and
$c(t)$ is the concentration of indicator appearing at the distal part and equal to $\phi_{xy}(t)$.

Since $h(t)$ is equivalent to the system impulse response and is a normalized statistical function, it has an area of one. Accordingly, the standard equation for flow is derived as follows:

$$h_3(t) = \frac{F}{q} \cdot c(t); \quad (6)$$

$$1 = \frac{F}{q} \cdot \int c(t);$$

$$F = \frac{q}{\int c(t)}.$$

Equation (6) is the classical equation for measuring cardiac output and is very similar to Equation (1).

In the Yelderman '974 patent a technique for determining the flow equation from the conservation of mass equation using stochastic processes was disclosed. For completeness, that derivation will be repeated in more detail here.

Heat capacity of blood, for example, is defined as $\Delta Q/\Delta T$. From the heat capacity the specific heat may be found as:

$$\frac{\text{heat capacity}}{\text{mass}} = \text{specific heat} = c = \frac{\Delta Q}{\Delta Q \cdot m}.$$

Rearranging the equation:

$$\Delta T = \frac{\Delta Q}{m \cdot c}, \quad (7)$$

where:
$\Delta Q$ = heat (cal);
$\Delta T$ = change in temperature (°C);
m = mass of the material (gms); and
c = specific heat (0.998 cal/gm/°C for water, 0.87 cal/gm/°C for blood).

By dividing Equation (7) by dt, a continuous or dynamic model results as follows:

$$\Delta T = \frac{\frac{d\Delta Q}{dt}}{\frac{dm}{dt} \cdot c}. \quad (8)$$

Since the quantity dm/dt may be defined as:

$$\frac{dm}{dt} = \gamma \cdot \rho \cdot \frac{dv}{dt},$$

where:
ρ is the density in gms/cc (1.0 gms/cc for water);
γ is the specific gravity (1.045 for blood); and
dv/dt is the flow in cc/sec,
Equation (8) may be changed to the following by substitution:

$$\Delta T = \frac{\frac{d\Delta Q}{dt} \text{(cal/sec)} \cdot 60 \text{(sec/min)}}{\frac{dm}{dt} \text{(1/min)} \cdot c \cdot \rho \cdot \gamma \cdot 1000 \text{(cc/1)}}. \quad (9)$$

Because it is desirous that the power be measured in watts, the conversion factor 1 cal/sec=4.18 watts is inserted, resulting in:

$$\Delta T(°C.) = \quad (10)$$

$$\frac{\frac{d\Delta Q \text{(watts * sec)}}{dt \text{(sec)}} \cdot 60 \frac{\text{(sec)}}{\text{(min)}} \cdot \frac{1\text{(cal)}}{4.18\text{(watts * sec)}}}{\frac{dv}{dt} \frac{(1)}{\text{(min)}} \cdot c \frac{\text{(cal)}}{\text{(gm*°C.)}} \cdot \rho \frac{\text{(gm)}}{\text{(cc)}} \cdot 1000 \frac{\text{(cc)}}{(1)} \cdot \gamma}.$$

Now by integrating both sides of Equation (10) with respect to time:

$$\int \Delta T \cdot \frac{dv}{dt} \cdot dt = \frac{60 \cdot \int \frac{d\Delta Q}{dt} \cdot dt}{c \cdot \rho \cdot \gamma \cdot 1000 \cdot 4.18}. \quad (11)$$

If one assumes that flow does not change during the time of the integration, then dv/dt is a constant and equals F, the average flow. Accordingly, the following substitution may be made:

$$\int \Delta T \cdot dt = \frac{60 \cdot \int \frac{d\Delta Q}{dt} \cdot dt}{c \cdot \rho \cdot \gamma \cdot 1000 \cdot 4.18 \cdot F}. \quad (12)$$

Rearranging Equation (12) results in:

$$\int \frac{d\Delta Q}{dt} \cdot dt \cdot 60 = F \cdot c \cdot \rho \cdot \gamma \cdot 1000 \cdot 4.18 \int \Delta T(t) \cdot dt. \quad (13)$$

Now for a stochastic input sequence to the heater, it is necessary to apply the definition of correlations. For this purpose, both sides of Equation (13) are multiplied by the unit code of 'a' and integrated:

$$\int \left( \lim_{T \to \infty} \frac{1}{2T} \int_{-T}^{+T} \frac{d\Delta Q(t)}{dt} \cdot a(t+\tau)dt \right) dt \cdot \frac{60}{4180} = \quad (14)$$

$$F \cdot c \cdot \rho \cdot \gamma \cdot \int \left( \lim_{T \to \infty} \frac{1}{2T} \int_{-T}^{+T} \Delta T(t) \cdot a(t+\tau)dt \right) dt.$$

The left side of equation (14) is evaluated first. The term $$\frac{d\Delta Q(t)}{dt}$$

is the heat applied at the input. Since only positive heat can be applied, the input is represented as a scalar times the code of +1, 0. That is:

$$\frac{d\Delta Q(t)}{dt} = P \cdot \bar{a}(t),$$

where P is the power applied.
Substituting, the following relationship follows:

$$P \cdot \int \left( \lim_{T \to \infty} \frac{1}{2T} \int_{-T}^{+T} \bar{a}(t) \cdot a(t+\tau)dt \right) dt \cdot \frac{60}{4180} = \quad (15)$$

$$F \cdot c \cdot \rho \cdot \gamma \cdot \int \left( \lim_{T \to \infty} \frac{1}{2T} \int_{-T}^{+T} \Delta T(t) \cdot a(t+\tau)dt \right) dt$$

The first integral term can be evaluated as follows, where 'a' has a value of 1:

$$\int \left( \lim_{T \to \infty} \frac{1}{2T} \int_{-T}^{+T} \bar{a}(t) \cdot a(t+\tau)dt \right) dt = \frac{(N+1) \cdot \Delta t}{N \cdot 2}.$$

By substituting:

$$P \cdot \frac{(N+1) \cdot \Delta t}{N \cdot 2} \cdot \frac{60}{4180} = \quad (16)$$

$$F \cdot c \cdot \rho \cdot \gamma \cdot \int \left( \lim_{T \to \infty} \frac{1}{2T} \int_{-T}^{+T} \Delta T(t) \cdot a(t+\tau)dt \right) dt.$$

The right side integral of Equation (14) may be evaluated as follows:

$$\int \left( \lim_{T \to \infty} \frac{1}{2T} \int_{-T}^{+T} \Delta T(t) \cdot a(t+\tau)dt \right) dt = \int \phi_{xy}(s)ds,$$

where $\phi_{xy}(s)$ is the cross-correlation between the unit code (+1,−1) and ΔT. For the discrete case, as for a PNS sequence, the following substitution may be made:

$$\int \phi_{xy}(s)ds = \Delta t \cdot \sum_{n=0}^{N-1} \phi_{xy}(n).$$

Making the final substitution:

$$P \cdot \frac{(N+1) \cdot \Delta t}{N \cdot 2} \cdot \frac{60}{4180} = F \cdot c \cdot \rho \cdot \gamma \cdot \Delta t \cdot \sum_{n=0}^{N-1} \phi_{xy}(n). \quad (17)$$

After rearranging, the flow equation set forth in the Yelderman '947 patent results:

$$F = \frac{(P/C) \cdot \frac{N+1}{N}}{\sum_{n=0}^{N-1} \phi_{xy}(n)} \text{ (1/min)}, \quad (18)$$

where:

-continued
$$C = \frac{4180 \cdot 2 \cdot c \cdot \rho \cdot \gamma}{60}.$$

Thus, Equation (18) directly relates volumetric flow to the cross-correlation function.

For purposes of the present application, Equation (18) may be restated as:

$$F_{td} = \frac{k_2}{\int_0^{NT_c} \phi_{xy}(s)ds}, \quad (19)$$

where:

$$k_2 = \frac{P}{C} \cdot \frac{N+1}{N}$$

and the cross-correlation function is expressed as an integral over the entire length of the input pseudorandom noise sequence, where N is the length of the input sequence and $T_c$ is the length of each bit duration in seconds. Equation (19) equals Equation (1) as expressed above.

As noted above, the area under the $\phi_{xy}(s)$ curve is inversely proportional to flow. However, in calculating the integral of the $\phi_{xy}(s)$ data (i.e., the area under the curve), the determination of the "DC" baseline offset and the determination of the amount of signal in the "tail" of the $\phi_{xy}(s)$ curve as it decreases into the baseline noise is not fully accounted for and results in error in the calculation. In other words, some error in the calculation of the area under the $\phi_{xy}(s)$ curve results because of the inaccuracy of the termination of the area under the $\phi_{xy}(s)$ curve as the curve exponentially decreases into the baseline noise as shown in FIG. 9. Since the overall volumetric flow can be represented as the calibration constant $k_2$ divided by the area under the $\phi_{xy}(s)$ curve, such errors in the calculation of the area under the $\phi_{xy}(s)$ curve result in errors in the determination of the flow.

The above-mentioned errors in the calculation of the area under the $\phi_{xy}(s)$ curve may be corrected by using the following technique to accurately determine the baseline and hence the area under the curve. The method used in accordance with the invention to determine the baseline first circularly rotates the $\phi_{xy}(s)$ data to the right by one $T_c$ period. Since the $\phi_{xy}(s)$ curve is equivalent to the convolution of a triangle function at the origin and the system's impulse response, rotating the $\phi_{xy}(s)$ data to the right by one $T_c$ period insures that the rising portion of the $\phi_{xy}(s)$ curve is to the right of the origin. The minimum value in the first two $T_c$ periods from the origin is then used as the baseline and subtracted from the $\phi_{xy}(s)$ curve to provide a curve $\phi_{xy}(s)'$.

The rising portion of the $\phi_{xy}(s)'$ data is then used to generate an ascending cumulative function from which an estimate of the effective standard deviation $\sigma$ is computed. This computation is made assuming that the rising portion of the $\phi_{xy}(s)'$ data was the left hand side of a Gaussian distribution function as in FIG. 9. The descending portion of the $\phi_{xy}(s)'$ data may then be plotted semilogarithmically (log $(\phi_{xy}(s)')$ vs. s) as shown in FIG. 12. The log $(\phi_{xy}(s)')$ data between $s_1 = \tau_{peak} + 2^*\sigma$ and $s_2 = s_1 + 2^*T_c$ (FIG. 9) is then fit to a straight line to determine the exponential decay constant $\tau$ as shown in FIG. 12. The area under the curve may then be computed:

$$\text{Area} = \sum_{s=0}^{s_2} \phi_{xy}(s)' + \tau \cdot \phi_{xy}(s_2). \quad (20)$$

The time domain flow estimate $F_{td}$ may then be calculated by dividing the area as determined by Equation (20) into $k_2$. Such a calculation has the benefit that the estimate of the area beyond $s_2$ (the second term of Equation (20)) provides considerable immunity to errors due to baseline noise and thus allows the tail of the $\phi_{xy}(s)$ curve to be more accurately estimated.

FREQUENCY DOMAIN FLOW ESTIMATION

The mathematical development of the basic time domain method for determining the flow estimate was set forth in the previous section. The basic frequency domain method will no be developed in accordance with the present invention, such a method having the benefit that phase data also may be used.

As set forth above, the area under the cross-correlation $\phi_{xy}(s)$ curve is inversely proportional to flow in a volumetric blood-flow estimate system. Given that x(t) is the input signal (heater element power) and y(t) is the output signal (thermistor temperature signal) of a linear system, the cross-correlation of x and y may be defined as:

$$\phi_{xy}(s) = \lim_{T \to \infty} \frac{1}{2T} \int_{-T}^{T} x(t) \cdot y(t + s)dt. \quad (21)$$

As a starting point, in a linear system with a system impulse response denoted by h(t) and with a single input signal x(t) and a single output signal y(t), the value of y(s) is given by the convolution integral:

$$y(s) = \int_0^T h(t) \cdot x(t - s)dt. \quad (22)$$

However, since the impulse response is zero for $t<0$, the lower limit of the convolution integral of Equation (22) may be changed to $-\infty$ without altering the identity. Also, since the impulse response is zero for increasing time, the upper limit can be extended to $\infty$ as well. Substituting the expression for y(t) in Equation (22) into Equation (21) to get the distribution function results in:

$$\phi_{xy}(s) = \quad (23)$$

$$\lim_{T \to \infty} \frac{1}{2T} \int_{-T}^{+T} x(t) \cdot \left[ \int_{-\infty}^{+\infty} h(v) \cdot x(t + s - v)dv \right] dt.$$

If x and y are continuous and of an exponential order, the order of the two limits can be reversed to obtain:

$$\phi_{xy}(s) = \quad (24)$$

$$\int_{-\infty}^{+\infty} h(v) \cdot \left[ \lim_{T \to \infty} \frac{1}{2T} \int_{-T}^{+T} x(t) \cdot y(t + s - v)dt \right] dv.$$

Since the term in brackets is simply the autocorrelation function $\phi_{xx}$ with an argument of $s-v$, Equation (24) may be expressed as:

$$\phi_{xy}(s) = \int_{-\infty}^{+\infty} h(t) \cdot \phi_{xx}(s - t)dt. \quad (25)$$

For the present invention, $\phi_{xy}(s)$ is proportional to a scaling factor which is the same as the "DC" component in the frequency domain. The "DC" component is determined by the area under the $\phi_{xy}(s)$ curve, namely, the area found in Equation (19). The scaling is incorporated into the present invention by allowing the input to be scaled as described below.

In particular, the impulse response of this system can be obtained by deconvolving Equation (25) for any given input x(t). Thus $$x(t) = \frac{k_3}{F} \bar{x}(t), \text{ where } k_3 = \frac{P}{\frac{4180}{60} \cdot \rho \cdot \gamma \cdot c} \quad (26)$$

and where $\bar{x}(t)$ equals the pseudorandom sequence input waveform (+1 or 0). Given that h(t) is both causal and of a finite duration, h(t)=0 for t<0 and t≧$NT_c$, then in the steady state (t>$NT_c$):

$$y(s) = \frac{k_3}{F} \int_0^{NT_c} h(t) \cdot \bar{x}(s - t)dt. \quad (27)$$

Cross-correlation of y(s), as set forth in Equation (27) with the autocorrelation of the input signal x(t), which equals 2(t)−1, provides:

$$\phi_{xy}(s) = \frac{k_3}{F} \int_0^{NT_c} h(t) \cdot \phi_{x\bar{x}}(s - t)dt. \quad (28)$$

Now, by taking the Fourier transform With respect to s of Equation (28), the cross-spectral density, $S_{xy}$, may be provided in terms of the system transfer function $H(\omega)$ and the spectral density of the input spectrum, $S_{xx}(\omega)$, as follows:

$$S_{xy}(\omega) = \frac{k_3}{F} H(\omega) \cdot S_{x\bar{x}}(\omega). \quad (29)$$

The cross-spectral density $S_{xy}(\omega)$ can be measured at each of the PNS harmonics by discrete Fourier transforming of the cross-correlation $\phi_{xy}$ at those frequencies by multiplying by a complex sinusoid as shown in FIG. 13(a) (for amplitude) and FIG. 13(b)(for phase). The input spectrum $S_{xx}$ can be similarly measured from $\phi_{xx}$ or defined by a theoretical expression with empirically equivalent results as shown in FIG. 14(a). If the system transfer function were known, the measurements of $S_{xy}$ and $S_{xx}$ and Equation (29) would allow the $S_{xy}/S_{xx}$ complex data to provide a flow estimate according to the following equation:

$$F(\omega) = k_3 \frac{H(\omega) \cdot S_{x\bar{x}}(\omega)}{S_{xy}(\omega)}, \quad (30)$$

where $\omega = \frac{n2\pi}{LT_c}$ for $n = 0$ to $L - 1$.

However, the transfer function $H(\omega)$ is in general unknown and depends on the physical catheter/circulatory system and the unknown flow. Thus, in accordance with the present invention, the frequency domain method is based upon the realization that a frequency domain representation of the "lagged normal" model developed by Bassingthwaighte et al. (used in the above derivation of the time domain model) can be used to extract the volumetric flow from the $S_{xy}/S_{x\bar{x}}$ data set.

As noted with respect to FIG. 9, the lagged normal impulse response is defined as the convolution of a truncated Gaussian (normal) function having three parameters, namely, the mean, $\mu$, the standard deviation, $\sigma$, and a decaying exponential having a time constant parameter $\tau$. Such a lagged normal impulse response function was calculated by Bassingthwaighte as noted above, but Bassingthwaighte did not have an exact expression for the lagged normal curve and instead generated it by passing the normal curve through a single pole difference equation. The present invention thus implements an exact expression for the lagged normal impulse response to directly relate the cross-correlation function to the volumetric flow. In addition, in accordance with the present invention an exact expression for the lagged normal transfer function has also been developed as well as an approximate expression for the transfer function. The exact expressions for the lagged normal transfer function used in accordance with the invention will be derived below.

As observed by Bassingthwaighte, the convolution of the normal Gaussian density curve with a first-order exponential process can be used to model the dispersion of an indicator in blood. In other words, the dispersion $h_3(t)$ equals:

$$h_3(t) = \int_0^t h_1(\lambda) \cdot h_2(t - \lambda)d\lambda. \quad (31)$$

Equation (31) can be converted to the frequency domain by taking its Fourier transform as follows:

$$\bar{h}_3(\omega) = \int_0^\infty dt\, e^{-j\omega t} \int_0^t h_1(\lambda) \cdot h_2(t - \lambda)d\lambda. \quad (32)$$

However, it is recognized by those skilled in the art that the convolution of two equations, as in Equation (31), in the time domain is equivalent to multiplication in the frequency domain. Then Equation (32) becomes:

$$\bar{h}_3(\omega) = \left[\int_0^\infty h_1(t)\, e^{-j\omega t}dt\right] \cdot \left[\int_0^\infty h_2(t)\, e^{-j\omega t}dt\right], \quad (33)$$

or for the lagged normal:

$$\bar{h}_3(\omega) = \left[\int_0^\infty \frac{1}{\tau} e^{\frac{-t}{\tau}} \cdot e^{-j\omega t}dt\right] \cdot \quad (34)$$

$$\left[\int_0^\infty \frac{1}{\sigma\sqrt{2\pi}} e^{-\frac{1}{2}(\frac{t-\mu}{\sigma})^2} \cdot e^{-j\omega t}dt\right].$$

For the first part, $$h_3(\omega) = \left[\int_0^\infty \frac{1}{\tau} e^{\frac{-t}{\tau}} \cdot e^{-j\omega t} dt\right] = \frac{1}{1+j\omega\tau}. \quad (35)$$

The Laplace transform for the second part may be found in any reference on the subject, but for this purpose, reference is made to *The Fast Fourier Transform and Its Applications*, by E. Oran Brigham, Prentice Hall, N.J., 1988, page 27. The Laplace transform may be found from:

$$\left(\frac{\alpha}{\pi}\right)^{\frac{1}{2}} e^{-\alpha t^2} \quad e^{\left(\frac{-\pi^2 f^2}{\alpha}\right)}$$

for the second part if the Gaussian is non-truncated and:

$$\alpha = \frac{1}{2\sigma^2} \text{ and } \omega^2 = 4\pi^2 f^2$$

and if the transform of a time delay, namely $\mu$, is $e^{-s\mu}$. Then the transform of the second part is:

$$\bar{h}_2(\omega) = \left[\int_0^\infty \frac{1}{\sigma\sqrt{2\pi}} e^{-\frac{1}{2}\left(\frac{t-\mu}{\sigma}\right)^2} \cdot e^{-j\omega t} dt\right] = e^{-\mu j\omega + .5(j\omega\sigma)^2}. \quad (36)$$

The final transform is thus as follows (including the effect of truncating the Gaussian for $t>0$):

$$\bar{h}_3(\omega) = \frac{1}{1+j\omega\tau} \cdot e^{-\mu j\omega + .5(j\omega\sigma)^2} \cdot \frac{erfc(jz)}{2}, \quad (37)$$

where *erfc* is the complementary error function and $$z = \omega\sigma/\sqrt{2} + j\mu/\sigma\sqrt{2}.$$

Equation (37) is the expression of the lagged normal transfer function in the frequency domain. From Equation (37) the amplitude and phase of the transfer function at a given frequency may be calculated as:

$$|\bar{h}_3(\omega)| = [u^2 + v^2]^{\frac{1}{2}} \quad (38)$$

and $$\text{phase} = \theta = -\tan^{-1}\left(\frac{v}{u}\right), \quad (39)$$

where u and v are the real and imaginary frequency components.

From Equations (2) and (3) an approximate lagged normal transfer function may be expressed as:

$$H(\omega) = \frac{e^{-j\omega\mu} \cdot e^{-2(\omega\sigma/2)^2}}{1+j\omega\tau}, \quad (40)$$

which represents the convolution of a nontruncated Gaussian with the decaying exponential. This transfer function may be used to estimate the volumetric flow in the frequency domain by defining a system identification cost function. Although a variety of cost functions may be used by those skilled in the art, it is presently preferred to define the system identification cost function using a real scalar C where:

$$C = \sum_{n=1}^{N} \left| \frac{S_{xy}(n)}{S_{x\bar{x}}(n)} - \frac{K_3}{F} H\left(\frac{2\pi n}{T_c}\right) \right|^2 \cdot SNR(n), \quad (41)$$

where SNR(n) is the output signal/noise ratio estimate at the nth code frequency of the pseudorandom signal (i.e., at one of the states of the pseudorandom signal) and where N corresponds to the number of input frequencies. In addition, SNR(n) is derived at each code frequency from a coherence function at each pseudorandom noise sequence harmonic frequency according to the following equation:

$$SNR(n) = \frac{P_{yy}(n\Omega) \cdot \gamma(n\Omega)}{\frac{1}{2}[P_{yy}((n-\frac{1}{2})\Omega) + P_{yy}((n+\frac{1}{2})\Omega)]} \quad (42)$$

where $\Omega = \frac{2\pi}{T_c}$ for $n = 1, 2, \ldots N$; and $P_{yy}$ is the power spectral of the output estimated using a discrete Fourier transform (DFT) with "boxcar" windows of length $2NT_c$ seconds.

The coherence function estimates $\gamma_n$ may be obtained using the same DFTs with a 75% overlap, for example. In other words, coherence function estimates are calculated from the cross-spectral density of the input and output signals as well as the input and output spectrums for each of the input frequencies.

The coherence function ranges from 0 to 1 depending on the amount that the heat input signal contributes to the measured temperature at the particular input frequency. The measured $P_{yy}$ and the coherence functions for a typical three minute segment of a signal plus human noise are shown in FIG. 14(b) for a spontaneously breathing patient. It should be observed that the error contribution to the cost function will be less for a low-frequency harmonic since the low-frequency noise decreases the measured coherence function.

The volumetric flow may then be estimated by using a nonlinear parameter estimation or curve fitting routine such as a Simplex algorithm or a Levinburg-Marquardt algorithm to adjust the unknown parameters $\sigma$, $\mu$, $\tau$, and $T_c$ until the scalar cost is minimized. As a result, the frequency domain flow estimate $F_{fd}$ may be defined as:

$$F_{fd} = F,$$

where C(F, $\mu$, $\sigma$ and $\tau$) is a minimum.

The results may be further improved by making several passes for the input data so that the lagged normal curve may be more easily approximated through simple averaging of the data from each pass. The number of such runs is dependent upon the amount of noise and the desired accuracy as well as the available time for an output reading.

DATA PROCESSING CIRCUITRY

An exemplary embodiment of a data processing apparatus for performing the processing functions described above in accordance with the invention is shown in detail in FIG. 15. It will be appreciated by those skilled in the art that the functional blocks shown may be implemented in software or in dedicated processing circuitry.

The signal processing circuitry of FIG. 15 primarily functions to fit against the lagged normal model developed above the temperature measurement data received from a thermistor mounted near the end of a Swan-Ganz balloon tipped catheter, for example, which is inserted through the jugular vein, floated through the right side of the heart and into the pulmonary artery, although other techniques are possible within the scope of the invention. Since the signal to noise ratio of such a heating system is typically −6 to 0 dB, the signal processing circuitry of the invention must be high-performance. In any event, as noted above, the lagged normal curve is a function of the time and distance between the input of the heat and the detection of the heat difference. As also noted above, the cross-correlation between the input and the output data depends on the amount of heat which is injected and the time which it takes for the heat to "wash out" of the area in which it mixes with the blood. As noted in the background portion of the specification, there was previously a lot of effort given at inputting the correct input into the system. The effect of such selection was to choose input so that the autocorrelation function allowed the output cross-correlation function to indicate the transfer function of the system. Such was the approach of the Yelderman '974 patent.

In the Yelderman '974 patent, a binary pseudorandom function, for example, was used as the input signal to provide broad band input energy, and in particular, to provide energy at discrete equally spaced frequencies. The autocorrelation of such a random signal is an isosceles triangle and is described in more detail by Davies, for example. However, when considering this signal in the frequency domain, as in the present invention, there are actually as many distinct frequencies as the code which is selected. For example, if the input code is 7, there are 7 frequencies. The same is true for any N frequencies inputted into the system, including a frequency of zero.

In the present invention, it is thus desired to calculate the transfer function of the system for virtually any inputs. For this purpose, the system of the invention cross-correlates the input signal with the output signal for purposes of generating the cross-correlation or "washout" curve (FIG. 9) and then solving the equation for the curve (derived above) to determine the flow. The area under the washout curve in the time domain is the same as the DC value on the $\bar{X}$-axis of its Fourier transform. Accordingly, by using frequencies which are spaced throughout the frequency range of the system, the flow may be calculated from the inverse of the area under the "washout" curve.

The above is accomplished in accordance with the present invention by inputting and getting the resulting DC amplitudes for different input frequencies, knowing that the washout curve in the frequency domain is the lagged normal curve which is generally identified by the Bassingthwaighte equation. Enough frequencies are thus input into the system so that the lagged normal curve may be fitted by the input frequencies. Theoretically, there is no requirement that more than about two or three input frequencies be used in the absence of noise to predict the frequency amplitude values. However, in reality there will not be a perfect fit to the lagged normal curve because of noise in the system. As a result, the present invention utilizes a coherence function to test the correlation of the input to the output for each of the frequencies in order to determine which ones are free of noise. A correlation value at or near one is highly correlated, while a value of less than one is poorly correlated and thus a highly noisy signal. This correlation can be done with a chirp, or as in a preferred embodiment, using a pseudorandom generator. In this manner, highly correlated input frequencies are selected in accordance with a correlation function so that the data may be more accurately fitted to the lagged normal curve.

In accordance with a preferred embodiment of the invention, a pseudorandom noise generator is used to provide 15 or more input frequencies in the form of binary codes. Fifteen frequencies are presently preferred, for as the number of input frequencies exceeds 15, the amount of input energy at each frequency goes down. Moreover, there is also the advantage of spacing the frequencies across the frequency band so that a broad band of interference will not knock out more than one frequency. A chirp signal having eight or more discrete frequencies across a 20 second time period would work for this purpose. In any event, in a real world environment at least seven frequencies must be used and weighted according to the degree of cross-correlation to receive adequate results.

Thus, the coherence function estimates may be found by forming a composite curve of seven or more curves which are offset a predetermined amount and added together or by entering the input frequencies sequentially, one after the other. Another approach is to use a continuous frequency (white noise) and then to calculate the coherence function by looking at bands of the white noise and calculating the coherence on each band. The determined coherence function estimates may then be used to calculate the proper weighting function (SNR) by squaring the coherence function estimates or using some other weighting scheme such as using the third or fourth powers of the coherence function estimates. The result is that any or all of the inputted frequencies may be ignored or weighted at any given time for purposes of fitting the received data to the lagged normal curve. Also, additional information may be determined from the phase and amplitude information of the curve.

The signal processing circuitry 100 of the invention will now be described with respect to FIG. 15. As shown, the received thermal noise is inputted into a pseudorandom noise sequence (PNS) parameter setup circuit 102 and analyzed to determine whether any fundamental noise frequencies are present in the thermal noise. If so, appropriate input frequencies are selected as described above to avoid interference between the thermal noise "glitches" and the inputted frequencies. The pseudorandom noise sequence (PNS) signal generator 104 receives this information and outputs the desired input signals (such as maximum length binary sequences). As described above, the number of input frequencies is preferably 15, although one skilled in the art may use other numbers of frequencies as desired.

The PNS generator output x'(t) (thermal power) is then inputted into the blood stream for thermal dilution flow measurement as indicated in FIG. 15 by block 106. Within the blood stream, the input signal is contaminated by thermal noise as indicated by adder 108 to provide the output signal y(t) actually detected by a thermistor downstream of the heating device on the catheter. The detected downstream signal y(t) is then inputted into the trend removal circuitry 110 to remove the low frequency drift of the received signal in the manner previously described. The output of the trend or low frequency drift removal circuit 110 is then inputted into noise event editor 112 to eliminate "bad" data caused by noise events such as coughing of the patient and excessive movement. The noise event editing may be accomplished by averaging the received data over the last several minutes of readings and then testing new data against the old averages in the manner generally described above. Data not within acceptable ranges will be removed.

The output of noise event editor 112 is then input along with the input signal x(t), a zero-mean reference phase PNS signal, into a polynomial cancelling cross-correlation device 114 so that the cross-correlation $\phi_{xy}(s)$ may be calculated as described above in Equation (28). The baseline of the cross-correlation function $\phi_{xy}(s)$ is then estimated by a baseline estimation circuit 116 as previously described so that the baseline may be subtracted from the cross-correlation function $\phi_{xy}(s)$ at summer 118 to provide a more accurate representation of the area under the $\phi_{xy}(s)$ curve (i.e., $\phi_{xy}(s)'$). The volumetric flow may then be calculated in the time domain in accordance with the technique previously described by inputting the resulting signal into circuits 120 and 122, which determine the amount of the signal under the $\phi_{xy}(s)$ curve, including the "tail" of the $\phi_{xy}(s)$ curve as it decreases into the baseline noise. In other words, Equation (1) is implemented in elements 120, 122, 124 and 126 by first determining the entire area under the lagged normal curve $(A_1+A_2=\phi_{xy}(s))$ at adder 124 (Equation (20)) and then determining the volumetric flow by taking the inverse of the area under the curve from adder 124 and multiplying the result at divider 126 by constant $k_2$, where $k_2$ has a value determined in accordance with Equation (19). The resulting time domain signal $F_{td}$ is then outputted and displayed as desired.

As noted above, in accordance with the invention the cross-correlation function may also be processed in the frequency domain by taking the discrete Fourier transform of the cross-correlation function $\phi_{xy}(s)$ at the PNS harmonics using discrete Fourier transform (DFT) circuit 128. The resulting cross-spectral density, $S_{xy}(\omega)$, is then divided by the input spectrum $S_{x\bar{x}}(\omega)$ at divider 130 in order to calculate the $S_{xy}/S_{x\bar{x}}$ data in accordance with Equation (30). This data is then used to fit the received data to the lagged normal distribution curve.

As noted above, in order to fit the received data to the lagged normal distribution curve, coherence function estimates must be obtained by taking the fast Fourier transforms (FFTs) of the input (x'(t)) and output (y(t)) signals at FFT 132 for frequencies having curves with a predetermined overlap such as 75%. The coherence function estimates $\gamma_n$ outputted by FFT 132 for each inputted frequency have values between 0 and 1 as noted above, and from these values, SNR weights are derived at SNR weight estimation circuit 134 for each harmonic frequency in the manner described above with respect to Equation (42), depending upon the amount of the heat input signal contribution to the measured temperature at that frequency. The resulting SNR weights and the $S_{xy}/S_{xx}$ data are then input into cost function calculation circuit 136 in order to determine the difference between the detected signal y(t) and the estimated lagged normal transfer function. The resulting error signal is then input into curve fitting circuitry 138 utilizing an algorithm such as a Simplex algorithm or a Levinburg-Marquardt estimation algorithm. The unknown parameters $\sigma$, $\tau$, $\mu$ and G needed to identify the lagged normal distribution curve are determined by the curve fitting algorithm of circuitry 138 and then used by the lagged normal transfer function ($H_3(\omega)$) circuit 140 to determine the gain adjusted lagged normal transfer function $G^*H_3(\omega)$ at multiplier 142 in accordance with Equation (37) and the output requirements. Finally, the output frequency $F_{fd}$ in the frequency domain is calculated by multiplying the output of lagged normal transfer function circuit 140 by constant $k_3$ at multiplier 144 (Equation 30), where constant $k_3$ is given in Equation (26). Accordingly, the output flow estimate $F_{fd}$ is identified as the flow estimate which most closely approximates the lagged normal distribution curve (i.e., the flow rate at which the function C(F, $\mu$, $\sigma$, $\tau$) is minimized). As with the time domain calculation, the volumetric flow estimate $F_{fd}$ may then be outputted and displayed as desired.

Obviously, the circuitry of FIG. 15 may be replaced by appropriate software under microprocessor control in accordance with the invention, whereby each element may be replaced by a processing block. Moreover, other data processing techniques for fitting the received data to the lagged normal distribution curve as herein determined are possible within the scope of the invention. Furthermore, other distribution curves for mathematically modeling the distribution of an indicator in a fluid may be used in accordance with the techniques herein described without departing from the teachings of the invention. Thus, although only an exemplary embodiment of the invention for use with a stochastic input heat bolus catheter arrangement and a lagged normal distribution model has been described in detail above, one skilled in the art will readily appreciate that many modifications are possible within the scope of the invention without materially departing from the novel teachings and advantages of the invention.

For example, although the approach described herein is empirical, those of ordinary skill in the art will understand that adaptive signal processing techniques also can be used. For example, algorithms or techniques can be added which allow automatic detection of the frequencies of interference and automatic selection of the pseudorandom sequences. Should the interfering frequencies change, the adaptive signal processing would allow for a change in the pseudorandom code. In addition, although pseudorandom binary sequences are used in the embodiment described, the use of stochastic input sources is not restricted or limited to these particular embodiments. Any input source can be used for which an autocorrelation can be computed. These and many other modifications of the present invention will be apparent to those of ordinary skill in the art. Accordingly, reference should be made only to the appended claims to determine the scope of this invention.

We claim:

1. A method of directly measuring volumetric flow of a fluid between a system entry point and a system exit point, comprising the steps of:

applying to said fluid, at said system entry point, a quantity of indicator under control of an excitation signal having a plurality of frequencies;

sensing a time-dependent response of said fluid to said excitation signal at said system exit point to obtain a response signal having a plurality of data points;

cross-correlating said excitation signal with said response signal to obtain a cross-correlation function signal representing cross-correlation data;

selecting a distribution function model which mathematically models the distribution of said indicator in said system;

comparing said cross-correlation data to said distribution function model;

adjusting said distribution function model to fit said cross-correlation data; and calculating a signal representative of volumetric flow of said fluid from said quantity of said indicator applied under control of said excitation signal and from said adjusted distribution function model.

2. The method according to claim 1, wherein said fluid is human blood.

3. The method according to claim 2, wherein said indicator is one of heat, cold, a dye, and a radioactive isotope added to said blood.

4. The method according to claim 1, wherein said excitation signal is a stochastic signal.

5. The method according to claim 4, wherein said stochastic signal is a pseudorandom maximum length binary sequence.

6. The method according to claim 1, wherein said excitation signal has at least three frequencies.

7. The method according to claim 6, wherein said excitation signal has fifteen frequencies.

8. The method according to claim 1, comprising the further steps of:

determining substantially noise-free and substantially noisy frequencies of said excitation signal;

calculating from said cross-correlation data weighting values for each frequency of said excitation signal, whereby said weighting values have values approaching one for said substantially noise-free frequencies of said excitation signal and values approaching zero for said substantially noisy frequencies of said excitation signal;

weighting said cross-correlation data with said weighting values so as to substantially eliminate the effect of received data at frequencies containing a predetermined amount of noise; and outputting said weighted cross-correlation function signal for use in said comparing step.

9. The method according to claim 8, wherein said weighting values calculating step comprises the steps of:

comparing input data at each frequency of said excitation signal with output data at each corresponding frequency component of said response signal;

selecting a coherence factor for each said frequency of said excitation signal, said coherence factor having a value approaching one when said output data is substantially noise-free at a particular frequency of said excitation signal, and a value approaching zero when said output data is substantially noisy at said particular frequency of said excitation signal; and determining said weighting values for each frequency of said excitation signal in accordance with said coherence factors.

10. The method according to claim 9, wherein said weighting values determining step includes the step of calculating said weighting values as the nth power of the values of said coherence factors, where n is at least 2.

11. The method according to claim 1, wherein said comparing step comprises the step of comparing said cross-correlation data to amplitude and phase functions of a lagged normal distribution function which mathematically models the distribution of said indicator in said system, and said adjusting step comprises the step of fitting said lagged normal distribution function to excitation signal - response function transfer function data, $S_{xy}/S_{x\bar{x}}$, by adjusting values of said lagged normal distribution function to fit said transfer function data.

12. The method according to claim 1, comprising the further steps of:

obtaining a background noise spectra of the system;

determining the frequencies of predominant noise amplitudes of the background noise spectra; and selecting said frequencies of said excitation signal so as to differ from said frequencies of said predominant noise amplitudes.

13. The method according to claim 12, wherein the step of determining the frequencies of predominant noise amplitudes of the background noise spectra comprises the step of taking a Fourier transform of the background noise spectra over multiple periods of the excitation signal.

14. The method according to claim 13, wherein said frequencies selecting step comprises the step of determining a clock time of the frequencies of said excitation signal such that said frequencies of predominant noise amplitudes of the background noise spectra are intermediate said frequencies of said excitation signal.

15. The method according to claim 1, comprising the further steps of:

(a) determining the average power of response signals resulting from the input of excitation signals comprising three adjacent pseudorandom noise sequences;

(b) fitting a quadratic curve to data points corresponding to the average power of said response signals resulting from the input of said three adjacent pseudorandom noise sequences;

(c) subtracting a portion of the fitted quadratic curve associated with the response signal for an intermediate pseudorandom noise sequence of said three adjacent pseudorandom noise sequences, data point by data point, from the response signal for said intermediate pseudorandom noise sequence so as to obtain drift adjusted response data;

(d) selecting three different adjacent pseudorandom noise sequences; and (e) repeating steps (a)-(d) for each of said selected three adjacent pseudorandom noise sequences so as to obtain a drift adjusted response signal.

16. The method according to claim 1, comprising the further steps of:

calculating an RMS value of the response signal for an excitation signal applied to said fluid;

calculating a mean, $RMS_{mean}$, and a standard deviation, $RMS_\sigma$, of said RMS value;

determining a threshold, $RMS_{th}$, according to the equation $RMS_{th} = RMS_{mean} + K*RMS_\sigma$, where K is a predetermined constant; and removing from said response signal data having an RMS value greater than $RMS_{th}$, thereby removing data from said response signal which was caused by an aberrant noise event of said system.

17. The method according to claim 1, wherein said excitation signal has a number of time and frequency intervals and comprises a number of data bits, and said calculating step comprises the step of generating said volumetric flow signal according to the expression:

$$F = \frac{k_2}{\int_0^{NT_c} \phi_{xy}(s)ds},$$

where: $k_2 = \frac{P}{C} \cdot \frac{N+1}{N}$ and

P is the rate of indicator infusion per unit time,
C is the specific density of the indicator volume in said fluid,
N is the number of time and frequency intervals in said excitation signal,
$T_c$ is the length of each data bit of said excitation signal,
$\phi_{xy}(s)$ is a cross-correlation curve representing the cross-correlation function signal over time, and
s is an integration variable.

18. The method according to claim 17, wherein said calculating step comprises the further step of calculating an area under the $\phi_{xy}(s)$ curve by performing the steps of:
advancing the $\phi_{xy}(s)$ curve by one $T_c$ period in the time domain;
determining a minimum value in the first two $T_c$ periods from a time origin of said $\phi_{xy}(s)$ curve as a baseline of said $\phi_{xy}(s)$ curve;
subtracting said baseline from said $\phi_{xy}(s)$ curve to provide a curve $\phi_{xy}(s)'$; and
calculating the area under the $\phi_{xy}(s)$ curve in accordance with the following expression:

$$\text{Area} = \sum_{s=0}^{s_2} \phi_{xy}(s)' + \tau \cdot \phi_{xy}(s_2),$$

where $s_2 = \tau_{peak} + 2^*\sigma + 2^*T_c$, $\sigma$ is the standard deviation of the $\phi_{xy}(s)'$ curve, $\tau_{peak}$ is the time of the peak of the $\phi_{xy}(s)'$ curve, and $\tau$ is an exponential decay constant of said $\phi_{xy}(s)'$ curve.

19. The method according to claim 1, wherein said calculating step comprises the step of generating said volumetric flow signal according to the expression:

$$F(\omega) = k_3 \frac{H(\omega) \cdot S_{xx}(\omega)}{S_{xy}(\omega)},$$

where
$\omega$ is each respective frequency of said excitation signal,
$k_3 = 2P/C$, P being the rate of indicator infusion per unit time, and C being the specific density of indicator volume in said fluid, where $C = 4180 \cdot 2 \cdot c \cdot \rho \cdot \gamma/60$, and where c is the specific heat for said fluid, $\rho$ is the density of said fluid, and $\gamma$ is the specific gravity of said fluid,
$H(\omega)$ is the transfer function of said system,
$S_{xx}(\omega)$ is the spectral density of said excitation signal, and
$S_{xy}(\omega)$ is the cross-spectral density of said excitation and response signals.

20. The method according to claim 19, wherein said transfer function $H(\omega)$ is represented as a lagged normal distribution equation for said indicator in said fluid.

21. The method according to claim 20, wherein said transfer function is expressed as:

$$H(\omega) = \frac{e^{-j\omega\mu}e^{-2(\omega\sigma/2)^2}}{1 + j\omega\tau},$$

where:
$\mu$ is a time delay of a Gaussian portion of a lagged normal curve corresponding to said lagged normal distribution equation,
$\sigma$ is the standard deviation of said lagged normal curve, and
$\tau$ is an exponential decay parameter of said lagged normal curve.

22. The method according to claim 19, wherein said excitation signal has a number of time and frequency intervals and comprises a number of data bits, and said calculating step further comprises the step of minimizing a system identification cost function using a real scalar C defined as:

$$C = \sum_{n=1}^{N} \left| \frac{S_{xy}(n)}{S_{x\bar{x}}(n)} - \frac{k_3}{F} H\left(\frac{2\pi n}{T_c}\right) \right|^2 \cdot SNR(n),$$

where:
N corresponds to the number of frequencies of said excitation signal,
$T_c$ is the length of each data bit of said excitation signal, and
SNR(n) is said weighting value for each frequency n of said excitation signal.

23. The method according to claim 22, wherein said step of minimizing a system identification cost function includes the step of deriving a value for SNR(n) at each frequency n of said excitation signal from a coherence function according to the following equation:

$$SNR(n) = \frac{P_{yy}(n\Omega) \cdot \gamma(n\Omega)}{\frac{1}{2}[P_{yy}((n-1)\Omega) + P_{yy}((n+1)\Omega)]},$$

where:
$P_{yy}$ is the power spectral density of the system output estimated using a discrete Fourier transform with windows of length $2NT_c$ seconds,
$\Omega = 2\pi/T_c$, and
$\gamma$ is a coherence function estimate of said excitation and response signals.

24. A method of directly measuring volumetric flow of a fluid between a system entry point and a system exit point, comprising the steps of:
applying to said fluid, at said system entry point, a quantity of indicator under control of an excitation signal having a plurality of frequencies;
sensing a time-dependent response of said fluid to said excitation signal at said system exit point to obtain a response signal having a plurality of data points;
cross-correlating said excitation signal with said response signal to obtain a cross-correlation function signal representing cross-correlation data;
determining substantially noise-free and substantially noisy frequencies of said excitation signal;
calculating from said cross-correlation data weighting values for each frequency of said excitation signal, whereby said weighting values have values approaching one for said substantially noise-free frequencies of said excitation signal and values approaching zero for said substantially noisy frequencies of said excitation signal;

weighting said cross-correlation data with said weighting values so as to substantially eliminate the effect of received data at frequencies containing a predetermined amount of noise; and calculating a signal representative of volumetric flow of said fluid from said weighted cross-correlation data and from said quantity of said indicator applied under control of said excitation signal.

25. The method according to claim 24, wherein said weighting values calculating step comprises the steps of:

comparing input data at each frequency of said excitation signal with output data at each corresponding frequency component of said response signal;

selecting a coherence factor for each said frequency of said excitation signal, said coherence factor having a value approaching one when said output data is substantially noise-free at a particular frequency of said excitation signal, and a value approaching zero when said output data is substantially noisy at said particular frequency of said excitation signal; and determining said weighting values for each frequency of said excitation signal in accordance with said coherence factors.

26. The method according to claim 25, wherein said weighting values determining step includes the step of calculating said weighting values as the nth power of the values of said coherence factors, where n is at least 2.

27. A method of directly measuring volumetric flow of a fluid between a system entry point and a system exit point, comprising the steps of:

obtaining a background noise spectra of the system;

determining the frequencies of predominant noise amplitudes of the background noise spectra;

selecting frequencies of an excitation signal so as to differ from said frequencies of said predominant noise amplitudes;

applying to said fluid, at said system entry point, a quantity of indicator under control of said excitation signal having said selected frequencies;

sensing a time-dependent response of said fluid to said excitation signal at said system exit point to obtain a response signal having a plurality of data points;

cross-correlating said excitation signal with said response signal to obtain a cross-correlation function signal representing cross-correlation data; and calculating a signal representative of volumetric flow of said fluid from said cross-correlation data and from said quantity of said indicator applied under control of said excitation signal.

28. The method according to claim 27, wherein the step of determining the frequencies of predominant noise amplitudes of the background noise spectra comprises the step of taking a Fourier transform of the background noise spectra over multiple periods of the excitation signal.

29. The method according to claim 28, wherein said frequencies selecting step comprises the step of determining a clock time of the frequencies of said excitation signal such that said frequencies of predominant noise amplitudes of the background noise spectra are intermediate said frequencies of said excitation signal.

30. A method of directly measuring volumetric flow of a fluid between a system entry point and a system exit point, comprising the steps of:

applying to said fluid, at said system entry point, a quantity of indicator under control of an excitation signal having a plurality of frequencies;

sensing a time-dependent response of said fluid to said excitation signal at said system exit point to obtain a response signal having a plurality of data points;

cross-correlating said excitation signal with said response signal to obtain a cross-correlation function signal representing cross-correlation data;

obtaining a background noise spectra of the system;

determining the frequencies of predominant noise amplitudes of the background noise spectra;

selecting said frequencies of said excitation signal so as to differ from said frequencies of said predominant noise amplitudes; and calculating a signal representative of volumetric flow of said fluid from said cross-correlation data and from said quantity of said indicator applied under control of said excitation signal at said selected frequencies.

31. The method according to claim 30, wherein the step of determining the frequencies of predominant noise amplitudes of the background noise spectra comprises the step of taking a Fourier transform of the background noise spectra over multiple periods of the excitation signal.

32. The method according to claim 31, wherein said frequencies selecting step comprises the step of determining a clock time of the frequencies of said excitation signal such that said frequencies of predominant noise amplitudes of the background noise spectra are intermediate said frequencies of said excitation signal.

33. A method of directly measuring volumetric flow of a fluid between a system entry point and a system exit point, comprising the steps of:

(a) applying to said fluid, at said system entry point, a quantity of indicator under control of excitation signals comprising three adjacent pseudorandom noise sequences;

(b) sensing a time-dependent response of said fluid to said excitation signals at said system exit point to obtain response signals having a plurality of data points;

(c) determining the average power of response signals resulting from the input of said three adjacent pseudorandom noise sequences;

(d) fitting a quadratic curve to data points corresponding to the average power of said response signals resulting from the input of said three adjacent pseudorandom noise sequences;

(e) subtracting a portion of the fitted quadratic curve associated with the response signal for an intermediate pseudorandom noise sequence of said three adjacent pseudorandom noise sequences, data point by data point, from the response signal for said intermediate pseudorandom noise sequence so as to obtain drift adjusted response data;

(f) selecting three different adjacent pseudorandom noise sequences;

(g) repeating steps (c)–(f) for each of said selected pseudorandom noise sequences so as to obtain a drift adjusted response signal;

(h) cross-correlating said excitation signal with said drift adjusted response signal to obtain a cross-correlation function signal representing cross-correlation data; and (i) calculating a signal representative of volumetric flow of said fluid from said cross-correlation data and from said quantity of said indicator applied under control of said excitation signal.

34. A method of directly measuring volumetric flow of a fluid between a system entry point and a system exit point, comprising the steps of:

applying to said fluid, at said system entry point, a quantity of indicator under control of an excitation signal having a plurality of frequencies;

sensing a time-dependent response of said fluid to said excitation signal at said system exit point to obtain a response signal having a plurality of data points;

removing from said response signal data representing an aberrant noise event so as to obtain a noise event edited response signal, said aberrant noise event data including a spike in said response signal having an abnormally large amplitude over a short time interval with respect to the remainder of said response signal;

cross-correlation said excitation signal with said noise event edited response signal to obtain a cross-correlation function signal representing cross-correlation data; and calculating a signal representative of volumetric flow of said liquid from said cross-correlation data and from said quantity of said indicator applied under control of said excitation signal.

35. The method according to claim 34, wherein said step of removing aberrant noise event data includes the steps of:

calculating an RMS value of the response signal for an excitation signal applied to said fluid;

calculating a mean, $RMS_{mean}$, and a standard deviation, $RMS_\sigma$, of said RMS value;

determining a threshold, $RMS_{th}$, according to the equation $RMS_{th} = RMS_{mean} + K*RMS_\sigma$, where K is a predetermined constant; and removing from said response signal data having an RMS value greater than $RMS_{th}$.

36. A method of directly measuring volumetric flow of a fluid between a system entry point and a system exit point, comprising the steps of:

applying to said fluid, at said system entry point, a quantity of indicator under control of an excitation signal having a plurality of frequencies;

sensing a time-dependent response of said fluid to said excitation signal at said system exit point to obtain a response signal having a plurality of data points;

cross-correlating said excitation signal with said response signal to obtain a cross-correlation function signal representing cross-correlation data; and calculating a signal representative of volumetric flow of said fluid from said quantity of said indicator applied under control of said excitation signal and from a transfer function of said system, wherein said calculating step comprises the step of generating said volumetric flow signal according to the expression:

$$F(\omega) = k_3 \frac{H(\omega) \cdot S_{xx}(\omega)}{S_{xy}(\omega)},$$

where:

$\omega$ is each respective frequency of said excitation signal, $k_3 = 2P/C$, P being the rate of indicator infusion per unit time, and C being the specific density of indicator volume in said fluid, where $C = 4180 \cdot 2 \cdot c \cdot \rho \cdot \gamma / 60$, and where c is the specific heat for said fluid, $\rho$ is the density of said fluid, and $\gamma$ is the specific gravity of said fluid, $H(\omega)$ is the transfer function of said system, $S_{xx}(\omega)$ is the spectral density of said excitation signal, and $S_{xy}(\omega)$ is the cross-spectral density of said excitation and response signals.

37. The method according to claim 36, wherein said transfer function $H(\omega)$ is represented as a lagged normal distribution equation for said indicator in said fluid.

38. The method according to claim 37, wherein said transfer function is expressed as:

$$H(\omega) = \frac{e^{-j\omega\mu_c - 2(\omega\sigma/2)^2}}{1 + j\omega\tau},$$

where:

$\mu$ is a time delay of a Gaussian portion of a lagged normal curve corresponding to said lagged normal distribution equation, $\sigma$ is the standard deviation of said lagged normal curve, and $\tau$ is an exponential decay parameter of said lagged normal curve.

39. The method according to claim 36, wherein said excitation signal has a number of time and frequency intervals and comprises a number of data bits, and said calculating step includes the further step of minimizing s system identification cost function using a real scalar C defined as:

$$C = \sum_{n=1}^{N} \left| \frac{S_{xy}(n)}{S_{x\bar{x}}(n)} - \frac{k_3}{F} H\left(\frac{2\pi n}{T_c}\right) \right|^2 \cdot SNR(n),$$

where:

N corresponds to the number of frequencies of said excitation signal, $T_c$ is the length of each data bit of said excitation signal, and $SNR(n)$ is said weighting value for each frequency n of said excitation signal.

40. The method according to claim 39, wherein said step of minimizing a system identification cost function includes the step of deriving a value for $SNR(n)$ at each frequency n of said excitation signal from a coherence function according to the following equation:

$$SNR(n) = \frac{P_{yy}(n\Omega) \cdot \gamma(n\Omega)}{\frac{1}{2}[P_{yy}((n-1)\Omega) + P_{yy}((n+1)\Omega)]}$$

where:

$P_{yy}$ is the power spectral density of the system output estimated using a discrete Fourier transform with windows of length $2NT_c$ seconds, $\Omega = 2\pi/T_c$, and $\gamma$ is a coherence function estimate of said excitation and response signals.

41. A method of directly measuring volumetric flow of a fluid between a system entry point and a system exit point, comprising the steps of:

(a) determining a distribution function model which mathematically model the distribution of an indicator in said system;

(b) applying to said fluid, at said system entry point, a quantity of said indicator under control of an excitation signal having a plurality of frequencies;

(c) sensing a time-dependent response of said fluid to said excitation signal at said system exit point to obtain a response signal having a plurality of data points;

(d) cross-correlating said excitation signal with said response signal to obtain a cross-correlation function signal representing cross-correlation data;

(e) comparing said cross-correlation data to said distribution function model;

(f) adjusting said distribution function model to fit said cross-correlation data;

(g) calculating a signal representative of volumetric flow of said fluid from said quantity of said indicator applied under control of said excitation signal and from said adjusted distribution model;

(h) repeating said steps (b) through (g) to produce a plurality of said volumetric flow signals; and (i) averaging said plurality of volumetric flow signals to produce an average volumetric flow signal.

42. An apparatus for directly measuring volumetric flow of a fluid between a system entry point and a system exit pint, comprising:

means for applying to said fluid, at said system entry point, a quantity of indicator under control of an excitation signal having a plurality of frequencies;

means for sensing a time-dependent response of said fluid to said excitation signal at said system exit point to obtain a response signal having a plurality of data points;

means for cross-correlating said excitation signal with said response signal to obtain a cross-correlation function signal representing cross-correlation data;

means for comparing said cross-correlation data to a distribution function model which mathematically models the distribution of said indicator in said system;

means for adjusting said distribution function model to fit said cross-correlation data; and means for calculating a signal representative of volumetric flow of said fluid from said quantity of said indicator applied under control of said excitation signal and from said adjusted distribution function model.

43. The apparatus of claim 42, wherein said fluid is human blood.

44. The apparatus of claim 43, wherein said indicator is one of heat, cold, a dye, and a radioactive isotope added to said blood.

45. The apparatus of claim 42, wherein said excitation signal is a stochastic signal.

46. The apparatus of claim 45, wherein said stochastic signal is a pseudorandom maximum length binary sequence.

47. The apparatus of claim 42, wherein said excitation signal has at least three frequencies.

48. The apparatus of claim 47, wherein said excitation signal has fifteen frequencies.

49. The apparatus of claim 42, further comprising:

means for determining substantially noise-free and substantially noisy frequencies of said excitation signal;

means for calculating from said cross-correlation data weighting values for each frequency of said excitation signal, whereby said weighting values have values approaching one for said substantially noise-free frequencies of said excitation signal and values approaching zero for said substantially noisy frequencies of said excitation signal;

means for weighting said cross-correlation data with said weighting values so as to substantially eliminate the effect of received data at frequencies containing a predetermined amount of noise; and means for outputting said weighted cross-correlation function signal to said comparing means.

50. The apparatus of claim 49, wherein said weighting values calculating means comprises weighting value processing means which performs the steps of:

comparing input data at each frequency of said excitation signal with output data at each corresponding frequency component of said response signal;

selecting a coherence factor for each said frequency of said excitation signal, said coherence factor having a value approaching one when said output data is substantially noise-free at a particular frequency of said excitation signal, and a value approaching zero when said output data is substantially noisy at said particular frequency of said excitation signal; and determining said weighting values for each frequency of said excitation signal in accordance with said coherence factors.

51. The apparatus of claim 50, wherein said weighting values calculating means calculates said weighting values as the nth power of the values of said coherence factors as said weighting values, where n is at least 2.

52. The apparatus of claim 42, wherein said comparing means compares said cross-correlation data to amplitude and phase functions of a lagged normal distribution function which mathematically models the distribution of said indicator in said system, and said adjusting means fits said lagged normal distribution function to excitation signal - response signal transfer function data, $S_{xy}/S_{xx}$, by adjusting values of said lagged normal distribution function to fit said transfer function data.

53. The apparatus of claim 42, further comprising setup means for obtaining a background noise spectra of the system, determining the frequencies of predominant noise amplitudes of the background noise spectra, and selecting said frequencies of said excitation signal so as to differ from said frequencies of said predominant noise amplitudes.

54. The apparatus of claim 53, wherein said setup means comprises means for taking a Fourier transform of the background noise spectra over multiple periods of the excitation signal for determining the frequencies of predominant noise amplitudes of the background noise spectra.

55. The apparatus of claim 54, wherein said setup means comprises means for determining a clock time of the frequencies of said excitation signal such that said frequencies of predominant noise amplitudes of the background noise spectra are intermediate said frequencies of said excitation signal.

56. The apparatus of claim 42, wherein said excitation signal comprises three adjacent pseudorandom noise sequences and said apparatus further comprises drift removal means including processing means for removing low frequency drift of said response signal by performing the steps of:

(a) determining the average power of response signals resulting from the input of said three adjacent pseudorandom noise sequences;

(b) fitting a quadratic curve to data points corresponding to the average power of said response signals resulting from the input of said three adjacent pseudorandom noise sequences;

(c) subtracting a portion of the fitted quadratic curve associated with the response signal for an intermediate pseudorandom noise sequence of said three adjacent pseudorandom noise sequences, data point by data point, from the response signal for said intermediate pseudorandom noise sequence so as to obtain drift adjusted response data;

(d) selecting three different adjacent pseudorandom noise sequences; and (e) repeating steps (a)–(d) for each of said selected three adjacent pseudorandom noise sequences so as to obtain a drift adjusted response signal.

57. The apparatus of claim 42, further comprising noise event editing means including processing means for performing the steps of:

calculating an RMS value of the response signal for an excitation signal applied to said fluid;

calculating a mean, $RMS_{mean}$, and a standard deviation, $RMS_\sigma$, of said RMS value;

determining a threshold, $RMS_{th}$, according to the equation $RMS_{th} = RMS_{mean} + K*RMS_\sigma$, where K is a predetermined constant; and removing from said response signal data having an RMS value greater than $RMS_{th}$, thereby removing data from said response signal which was caused by an aberrant noise event of said system.

58. The apparatus of claim 42, wherein said excitation signal has a number of time and frequency intervals and comprises a number of data bits, and said calculating means comprises processing means for generating said volumetric flow signal according to the expression:

$$F = \frac{k_2}{\int_0^{NT_c} \phi_{xy}(s)ds},$$

where: $k_2 = \frac{P}{C} \cdot \frac{N+1}{N}$ and

P is the rate of indicator infusion per unit time,

C is the specific density of the indicator volume in said fluid,

N is the number of time and frequency intervals in said excitation signal, $T_c$ is the length of each data bit of said excitation signal, $\phi_{xy}(s)$ is a cross-correlation curve representing the cross-correlation function signal over time, and s is an integration variable.

59. The apparatus of claim 58, wherein said processing means further calculates an area under the $\phi_{xy}(s)$ curve by performing the steps of:

advancing the $\phi_{xy}(s)$ curve by one $T_c$ period in the time domain;

determining a minimum value in the first two $T_c$ periods from a time origin of said $\phi_{xy}(s)$ curve as a baseline of said $\phi_{xy}(s)$ curve;

subtracting said baseline from said $\phi_{xy}(s)$ curve to provide a curve $\phi_{xy}(s)'$; and calculating the area under the $\phi_{xy}(s)$ curve in accordance with the following expression:

$$\text{Area} = \sum_{s=0}^{s_2} \phi_{xy}(s)' + \tau \cdot \phi_{xy}(s_2),$$

where $s_2 = \tau_{peak} + 2*\sigma + 2*T_c$, $\sigma$ is the standard deviation of the $\phi_{xy}(s)'$ curve, $\tau_{peak}$ is the time of the peak of the $\phi_{xy}(s)'$ curve, and $\tau$ is an exponential decay constant of said $\phi_{xy}(s)'$ curve.

60. The apparatus of claim 42, wherein said calculating means comprises means for generating said volumetric flow signal according to the expression:

$$F(\omega) = k_3 \frac{H(\omega) \cdot S_{xx}(\omega)}{S_{xy}(\omega)},$$

where $\omega$ is each respective frequency of said excitation signal, $k_3 = 2P/C$, P being the rate of indicator infusion per unit time, and C being the specific density of indicator volume in said fluid, where $C = 4180 \cdot 2 \cdot c \cdot \rho \cdot \gamma/60$, and where c is the specific heat for said fluid, $\rho$ is the density of said fluid, and $\gamma$ is the specific gravity of said fluid, $H(\omega)$ is the transfer function of said system, $S_{xx}(\omega)$ is the spectral density of said excitation signal, and $S_{xy}(\omega)$ is the cross-spectral density of said excitation and response signals.

61. The apparatus of claim 60, wherein said transfer function $H(\omega)$ is represented as a lagged normal distribution equation for said indicator in said fluid.

62. The apparatus of claim 61, wherein said transfer function is expressed by said generating means as:

$$H(\omega) = \frac{e^{-j\omega\mu}e^{-2(\omega\sigma/2)^2}}{1 + i\omega\tau},$$

where:

$\mu$ is a time delay of a Gaussian portion of a lagged normal curve corresponding to said lagged normal distribution equation, $\sigma$ is the standard deviation of said lagged normal curve, and $\tau$ is an exponential decay parameter of said lagged normal curve.

63. The apparatus of claim 60, wherein said excitation signal has a number of time and frequency intervals and comprises a number of data bits, and said means for generating said volumetric flow signal comprises means for minimizing a system identification cost function using a real scalar C defined as:

$$C = \sum_{n=1}^{N} \left| \frac{S_{xy}(n)}{S_{xx}(n)} - \frac{k_3}{F} H\left(\frac{2\pi n}{T_c}\right) \right|^2 \cdot SNR(n),$$

where:

N corresponds to the number of frequencies of said excitation signal, $T_c$ is the length of each data bit of said excitation signal, and SNR(n) is said weighting value for each frequency n of said excitation signal.

64. The apparatus of claim 63, wherein said minimizing means comprises means for deriving a value for SNR(n) for each frequency n of said excitation signal from a coherence function according to the following equation:

$$SNR(n) = \frac{P_{yy}(n\Omega) \cdot \gamma(n\Omega)}{\frac{1}{2}[P_{yy}((n-\frac{1}{2})\Omega) + P_{yy}((n+\frac{1}{2})\Omega)]}$$

where:
- $P_{yy}$ is the power spectral density of the system output estimated using a discrete Fourier transform with windows of length $2NT_c$ seconds,
- $\Omega = 2\pi/T_c$, and
- $\gamma$ is a coherence function estimate of said excitation and response signals.

65. An apparatus for directly measuring volumetric flow of a fluid between a system entry point and a system exit point, comprising:
- means for applying to said fluid, at said system entry point, a quantity of indicator under control of an excitation signal having a plurality of frequencies;
- means for sensing a time-dependent response of said fluid to said excitation signal at said system exit point to obtain a response signal having a plurality of data points;
- means for cross-correlating said excitation signal with said response signal to obtain a cross-correlation function signal representing cross-correlation data;
- means for determining substantially noise-free and substantially noisy frequencies of said excitation signal;
- means for calculating from said cross-correlation data weighting values for each frequency of said excitation signal, whereby said weighting values have values approaching one for said substantially noise-free frequencies of said excitation signal and values approaching zero for said substantially noisy frequencies of said excitation signal;
- means for weighting said cross-correlation data with said weighting values so as to substantially eliminate the effect of received data at frequencies containing a predetermined amount of noise; and
- means for calculating a signal representative of volumetric flow of said fluid from said weighted cross-correlation data and from said quantity of said indicator applied under control of said excitation signal.

66. The apparatus of claim 65, wherein said weighting values calculating means comprises:
- means for comparing input data at each frequency of said excitation signal with output data at each corresponding frequency component of said response signal;
- means for selecting a coherence factor for each said frequency of said excitation signal, said coherence factor having a value approaching one when said output data is substantially noise-free at a particular frequency of said excitation signal, and a value approaching zero when said output data is substantially noisy at said particular frequency of said excitation signal; and
- means for determining said weighting values for each frequency of said excitation signal in accordance with said coherence factors.

67. The apparatus of claim 66, wherein said weighting values determining means includes means for calculating said weighting values as the nth power of the values of said coherence factors, where n is at least 2.

68. An apparatus for directly measuring volumetric flow of a fluid between a system entry point and a system exit point, comprising:
- setup means for obtaining a background noise spectra of the system, determining the frequencies of predominant noise amplitudes of the background noise spectra, and selecting frequencies of an excitation signal so as to differ from said frequencies of said predominant noise amplitudes;
- means for applying to said fluid, at said system entry point, a quantity of indicator under control of said excitation signal having said selected frequencies;
- means for sensing a time-dependent response of said fluid to said excitation signal at said system exit point to obtain a response signal having a plurality of data points;
- means for cross-correlating said excitation signal with said response signal to obtain a cross-correlation function signal representing cross-correlation data; and
- means for calculating a signal representative of volumetric flow of said fluid from said cross-correlation data and from said quantity of said indicator applied under control of said excitation signal.

69. The apparatus of claim 68, wherein said setup means comprises means for taking a Fourier transform of the background noise spectra over multiple periods of the excitation signal for determining the frequencies of predominant noise amplitudes of the background noise spectra.

70. The apparatus of claim 69, wherein said setup means comprises means for determining a clock time of the frequencies of said excitation signal such that said frequencies of predominant noise amplitudes of the background noise spectra are intermediate said frequencies of said excitation signal.

71. An apparatus for directly measuring volumetric flow of a fluid between a system entry point and a system exit point, comprising:
- means for applying to said fluid, at said system entry point, a quantity of indicator under control of excitation signals comprising three adjacent pseudorandom noise sequences;
- means for sensing a time-dependent response of said fluid to said excitation signals at said system exit point to obtain response signals having a plurality of data points;
- drift removal means including processing means for removing low frequency drift of said response signal by performing the steps of:
  (a) determining the average power of response signals resulting from the input of said three adjacent pseudorandom noise sequences;
  (b) fitting a quadratic curve to points corresponding to the average power of said response signals resulting from the input of said three adjacent pseudorandom noise sequences;
  (c) subtracting a portion of the fitted quadratic curve associated with the response signal for an intermediate pseudorandom noise sequence of said three adjacent pseudorandom noise sequences, data point by data point, from the response signal for said intermediate pseudorandom noise sequence so as to obtain drift adjusted response data;

(d) selecting three different adjacent pseudorandom noise sequences; and (e) repeating steps (a)–(d) for each of said selected pseudorandom noise sequences so as to obtain a drift adjusted response signal;

means for cross-correlating said excitation signal with said drift adjusted response signal to obtain a cross-correlation function signal representing cross-correlation data; and means for calculating a signal representative of volumetric flow of said fluid from said cross-correlation data and from said quantity of said indicator applied under control of said excitation signal.

72. An apparatus for directly measuring volumetric flow of a fluid between a system entry point and a system exit point, comprising:

means for applying to said fluid, at said system entry point, a quantity of indicator under control of an excitation signal having a plurality of frequencies;

means for sensing a time-dependent response of said fluid to said excitation signal at said system exit point to obtain a response signal having a plurality of data points;

means for removing from said response signal data representing an aberrant noise event so as to obtain a noise event edited response signal, said aberrant noise event data including a spike in said response signal having an abnormally large amplitude over a short time interval with respect to the remainder of said response signal;

means for cross-correlating said excitation signal with said noise event edited response signal to obtain a cross-correlation function signal representing cross-correlation data; and means for calculating a signal representative of volumetric flow of said fluid from said cross-correlation data and from said quantity of said indicator applied under control of said excitation signal.

73. The apparatus of claim 72, wherein said aberrant noise event removing means comprises:

processing means for performing the steps of:

calculating an RMS value of the response signal for an excitation signal applied to said fluid, calculating a mean, $RMS_{mean}$, and a standard deviation, $RMS_\sigma$, of said RMS value, and determining a threshold, $RMS_{th}$, according to the equation $RMS_{th} = RMS_{mean} + K*RMS_\sigma$, where K is a predetermined constant; and means for removing from said response signal data having an RMS value greater than $RMS_{th}$.

74. An apparatus for directly measuring volumetric flow of a fluid between a system entry point and a system exit point, comprising:

means for applying to said fluid, at said system entry point, a quantity of indicator under control of an excitation signal having a plurality of frequencies;

means for sensing a time-dependent response of said fluid to said excitation signal at said system exit point to obtain a response signal having a plurality of data points;

means for cross-correlating said excitation signal with said response signal to obtain a cross-correlation function signal representing cross-correlation data; and means for calculating a signal representative of volumetric flow of said fluid from said quantity of said indicator applied under control of said excitation signal and from a transfer function of said system, said calculating means comprising processing means for generating said volumetric flow signal according to the expression:

$$F(\omega) = k_3 \frac{H(\omega) \cdot S_{xx}(\omega)}{S_{xy}(\omega)},$$

where:

$\omega$ is each respective frequency of said excitation signal, $k_3 = 2P/C$, P being the rate of indicator infusion per unit time, and C being the specific density of indicator volume in said fluid, where $C = 4180 \cdot 2 \cdot c \cdot \rho \cdot \gamma / 60$, and where c is the specific heat for said fluid, $\rho$ is the density of said fluid, and $\gamma$ is the specific gravity of said fluid, $H(\omega)$ is the transfer function of said system, $S_{xx}(\omega)$ is the spectral density of said excitation signal, and $S_{xy}(\omega)$ is the cross-spectral density of said excitation and response signals.

75. The apparatus of claim 74, wherein said transfer function $H(\omega)$ is represented as a lagged normal distribution equation for said indicator in said fluid.

76. The apparatus of claim 75, wherein said transfer function is expressed by said processing means as:

$$H(\omega) = \frac{e^{-j\omega\mu} e^{-2(\omega\sigma/2)^2}}{1 + i\omega\tau},$$

where:

$\mu$ is a time delay of a Gaussian portion of a lagged normal curve corresponding to said lagged normal distribution equation, $\sigma$ is the standard deviation of said lagged normal curve, and $\tau$ is an exponential decay parameter of said lagged normal curve.

77. The apparatus of claim 74, wherein said excitation signal has a number of time and frequency intervals and comprises a number of data bits, and said processing means comprises means for minimizing a system identification cost function using a real scalar C defined as:

$$C = \sum_{n=1}^{N} \left| \frac{S_{xy}(n)}{S_{xx}(n)} - \frac{k_3}{F} H\left(\frac{2\pi n}{T_c}\right) \right|^2 \cdot SNR(n),$$

where:

N corresponds to the number of frequencies of said excitation signal, $T_c$ is the length of each data bit of said excitation signal, and SNR(n) is said weighting value for each frequency n of said excitation signal.

78. The apparatus of claim 77, wherein said minimizing means comprises means for deriving a value for SNR(n) for each frequency n of said excitation signal from a coherence function according to the following equation:

$$SNR(n) = \frac{P_{yy}(n\Omega) \cdot \gamma(n\Omega)}{\frac{1}{2}[P_{yy}((n-1)\Omega) + P_{yy}((n+1)\Omega)]}$$

where:

$P_{yy}$ is the power spectral density of the system output estimated using a discrete Fourier transform with windows of length $2NT_c$ seconds, $\Omega = 2\pi/T_c$, and $\gamma$ is a coherence function estimate of said excitation and response signals.

79. An apparatus for directly measuring volumetric flow of a fluid between a system entry point and a system exit point, comprising:

means for repeatedly applying to said fluid, at said system entry point, a quantity of indicator under control of an excitation signal having a plurality of frequencies;

means for sensing a time-dependent response of said fluid to said excitation signal at said system exit point to obtain a response signal having a plurality of data points;

means for cross-correlating said excitation signal with said response signal to obtain a cross-correlation function signal representing cross-correlation data;

means for determining a distribution function model which mathematically models the distribution of an indicator in said system and for comparing said cross-correlation data to said distribution function model;

means for adjusting said distribution function model to fit said cross-correlation data;

means for calculating a signal representative of volumetric flow of said fluid from said quantity of said indicator applied under control of said excitation signal and from said adjusted distribution function model for each application of said quantity of said indicator; and means for averaging said volumetric flow signals for each application of said quantity of said indicator to produce an average volumetric flow signal.

* * * * *